United States Patent [19]

Takematsu et al.

[11] Patent Number: 4,491,465

[45] Date of Patent: Jan. 1, 1985

[54] SUBSTITUTED PHENYL (THIONO)CARBAMATES, HERBICIDAL COMPOSITIONS CONTAINING THE SAME AS ACTIVE INGREDIENT AND METHOD OF CONTROLLING WEEDS

[75] Inventors: Tetsuo Takematsu; Makoto Konnai, both of Utsunomiya; Takeo Hosogai; Takashi Nishida, both of Kurashiki, all of Japan

[73] Assignee: Kuraray Co., Ltd., Kurashiki, Japan

[21] Appl. No.: 378,221

[22] Filed: May 14, 1982

[30] Foreign Application Priority Data

May 19, 1981 [JP] Japan .................................. 56-76198
Jul. 13, 1981 [JP] Japan ................................ 56-109787

[51] Int. Cl.$^3$ ...................... A01N 43/36; A01N 43/40; C07D 211/68; C07D 207/00
[52] U.S. Cl. ............................................ 71/88; 71/90; 71/94; 71/95; 544/106; 546/226; 548/201; 548/531; 260/239 BE; 260/239 BF
[58] Field of Search ............... 71/95, 94, 88; 548/531; 546/226; 260/239 BE, 239 BF

[56] References Cited

U.S. PATENT DOCUMENTS

| | | | |
|---|---|---|---|
| 3,217,002 | 11/1965 | Weiss | 548/531 X |
| 3,224,862 | 12/1965 | Weiss | 548/531 X |
| 3,224,864 | 12/1965 | Hamm et al. | 548/531 X |
| 3,462,453 | 8/1969 | Popoff et al. | 71/95 |
| 3,863,474 | 2/1975 | Kudamatsu et al. | 71/95 X |
| 4,153,446 | 5/1979 | Schneider et al. | 71/95 |
| 4,165,976 | 8/1979 | King | 71/95 X |
| 4,361,438 | 11/1982 | Felix | 71/94 X |

FOREIGN PATENT DOCUMENTS 57-130968  8/1982  Japan ..................................... 71/95

*Primary Examiner*—Joseph Paul Brust
*Attorney, Agent, or Firm*—Burns, Doane, Swecker & Mathis

[57] ABSTRACT

There are provided novel substituted phenyl (thiono)carbamates capable of effectively controlling broad-leaved annual weeds and annual weeds belonging to the families Gramineae and Cyperaceae such as wild Echinochloa species, monochoria, toothcup and umbrella plant, herbicidal compositions containing these (thiono)carbamates as active ingredient and a method of controlling weeds using these (thiono)carbamates. The (thiono)carbamates are substantially nonphytotoxic to useful crop plants such as the paddy rice plant.

42 Claims, No Drawings

SUBSTITUTED PHENYL (THIONO)CARBAMATES, HERBICIDAL COMPOSITIONS CONTAINING THE SAME AS ACTIVE INGREDIENT AND METHOD OF CONTROLLING WEEDS

BACKGROUND OF THE INVENTION

1. Field of the Invention

This invention relates to novel substituted phenyl carbamates and thionocarbamates [hereinafter collectively called "substituted phenyl (thiono)carbamates"] represented by the general formula (I)

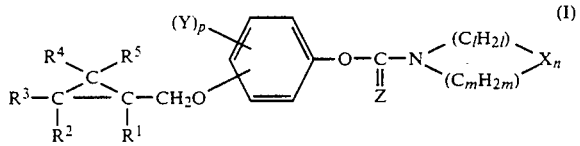

wherein X is an oxygen or sulfur atom or a vinylene group, l and m each is an integer of 1 to 4, n is an integer of 0 or 1, the heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, $R^4$ and $R^5$ are the same or different and each is a halogen atom and Z is an oxygen or sulfur atom; herbicidal compositions containing the same as active ingredients and a method of controlling weeds using said substituted phenyl (thiono)carbamates.

2. Description of the Prior Art

It is known that certain substituted phenyl carbamates, such as 4-chlorophenyl 1-pyrrolidinecarboxylate and 2,4-dichlorophenyl 1-pyrrolidinecarboxylate, can inhibit the growth of weeds on the cultivated field in pre-emergence application and can selectively control Echinochloa species (barnyard grass, etc.) at their growth stage in the paddy field (cf. U.S. Pat. No. 3,142,556 and Japanese Patent Application Publication No. 17,157/1971). However, these substituted phenyl carbamates are not so satisfactory in their herbicidal activity. Certain substituted phenyl thionocarbamates, such as O-(4-chlorophenyl) 1-pyrrolidinecarbothioate and O-(3-methoxyphenyl) 1-pyrrolidinecarbothioate, are also known to be herbicidally active against weeds on the cultivated field (cf. U.S. Pat. No. 3,217,002). However, these substituted phenyl thionocarbamates are impracticable because of their insufficient herbicidal activity and strong phytotoxicity to the desired crop plants.

SUMMARY OF THE INVENTION

An object of the invention is to provide substituted phenyl (thiono)carbamates of general formula (I) which have high herbicidal activity against a variety of weeds, herbicidal compositions containing said substituted phenyl (thiono)carbamates as active ingredient and a method of controlling various weeds using said substituted phenyl (thiono)carbamates.

Another object of the invention is to provide substituted phenyl (thiono)carbamates of the above general formula (I) which are remarkably superior to the so far known substituted phenyl carbamates and substituted phenyl thionocarbamates especially in herbicidal activity against broad-leaved annual weeds and against annual weeds belonging to the families Gramineae and Cyperaceae.

A further object of the invention is to provide substituted phenyl (thiono)carbamates of the above general formula (I) which are almost nonphytotoxic to useful crop plants such as the paddy rice plant.

DETAILED DESCRIPTION OF THE INVENTION

In the above general formula (I), X is an oxygen or sulfur atom or a vinylene group, l and m each is an integer of 1 to 4 and n is an integer of 0 or 1. The heterocycle comprising the nitrogen atom, the two alkylene chains and X is 5- to 7-membered, and the two alkylene chains each may be branched. From the viewpoint of herbicidal activity, the heterocycle moiety of the substituted phenyl (thiono)carbamates of general formula (I) is preferably 5-membered or 6-membered. Y is a halogen atom such as a fluorine, chlorine or bromine atom, and p is an integer of 1 or 2. $R^1$ is a hydrogen atom or a lower alkyl group such as methyl, ethyl, propyl or butyl, $R^2$ and $R^3$ are the same or different and each is a hydrogen atom, a lower alkyl group such as methyl, ethyl, propyl or butyl, or a phenyl group, and $R^4$ and $R^5$ are the same or different and each is a halogen atom such as a fluorine, chlorine or bromine atom. Z is an oxygen or sulfur atom.

It has now been found that the substituted phenyl (thiono)carbamates of the above general formula (I) have high herbicidal activity against a variety of weeds, are remarkably superior to the above-mentioned known substituted phenyl carbamates and substituted phenyl thionocarbamates especially in herbicidal activity against broad-leaved annual weeds and against annual weeds belonging to the families Gramineae and Cyperaceae and are substantially nonphytotoxic to useful crop plants such as the paddy rice plant.

The substituted phenyl (thiono)carbamates of general formula (I) are herbicidally active against weeds growing undesirably in such places as rice paddy fields and upland cultivated fields, for example *Elatine triandra* SCHK. (long stemmed water-wort), *Ammannia multiflora* ROXB. (red stem), *Rotala indica* KOEHNE (toothcup), *Rotala pusilla* TULASNE, *Ludwigia prostrata* ROXB. (false loosestrife), *Euphorbia supina* RAFIN (milk purslane), *Euphorbia pseudochamaesyce* FISCH. MEY. et LALLEM. (Garten-wolfsmilch), *Acalypha australis* L. (virginia copperleaf), *Fatoua villosa* NAKAI, *Chenopodium ficifolium* SMITH, *Amaranthus lividus* L. (wild amaranth), *Portulaca oleracea* L. (common purslane), *Mollugo stricta* L., *Sagina japonica* OHWI (pearlwort), *Polygonum Hydropiper* L. (water pepper), *Polygonum persicaria* L. (pink persicaria), *Polygonum lapathifolium* L. (pale-persicaria), *Polygonum longisetum* DE BRUYN, *Polygonum lapathifolium* L. subsp. nodosum KITAM., *Polygonum aviculare* L. (knot-grass), *Polygonum nepalense* MEISN, *Deicnostema violaceum* YAMAZAKI, *Dopatrium junceum* HAMILT., *Lindernia pyxidaria* L. (false pimpernel), *Vandellia anqustifolia* BENTH., *Deinstema violacea* YAMAZAKI, *Mazus japonicus* O. KUNTZE, *Mazus Miquelii* MAKINO, *Bothriospermum tenellum* FISCH. et MEY., *Trigonotis peduncularis* BENTH., *Mosla dianthera* MAXIM., *Lobelia chinensis* LOUR. (lobelia), *Erigeron annuus* PERS (annual fleabane), *Eclipta prostrata* L. (American false daisy), *Bidens tripartita* L.

(erect bur marigold), *Bidens frondosa* L. (devils beggarticks), *Centipeda minima* A. BRAUN. et ASCHERS (spreading sneezeweed), *Galinsoga ciliata* BLAKE (hairy galinsoga) and other dicotyledonous weeds; *Sagittaria aginashi* MAKINO, *Alisma canaliculatum* A. BR. et BOUCHÉ,*Aneilema Keisak* HASSK, *Commelina communis* L. (Asiatic dayflower), *Eriocaulon Sieboldtianum* SIEB. et ZUCC. (pipewort), *Monochoria vaginalis* PRESL (monochoria), *Cyperus microiria* STEUD. (flat sedge), *Cyperus Iria* L. (yellow-cyperus), *Lipocarpha microcephala* KUNTH, *Cyperus difformis* L. (umbrella plant), *Cyperus haspan* L., *Cyperus hakonensis* PRANCH. et SAVAT., *Cyperus sanguinolentus* VAHL, *Eleocharis pellucida* PRESL (spikerush), *Fimbristylis dichotoma* VAHL (fimbristylis), *Fimbristylis autumnalis* ROEM. et SCHULT. (autumn rush), *Scirpus juncoides* ROXB. (hardstem bulrush), *Fimbristylis miliacea* VAHL, *Cyperus serotinus* ROTTB., *Kyringa brevifolia* ROTTB. subsp. *leiolepis* T. KOYAMA (green kyllinga), *Eleocharis acicularis* ROEM. et SCHULT. (slender spikerush), *Scirpus maritimus* L. (sea clubrush), *Echinochloa Crus galli* BEAUV. typica HONDA. (watergrass), *Echinochloa oryzicola* VASING., *Echinochloa crus-galli* BEAUX. (cockspur-grass), *Beckmannia syzigachne* FERNALD (Beckmann's grass), *Digitaria adscendens* HENR. (large crab-grass), *Eleusine indica* GAERTN. (goose grass), *Setaria viridis* BEAUV. (green panicum), *Setaria glauca* BEAUV. (glaucous panicum) and other monocotyledonous weeds. They have remarkably high eradicative activity especially against those wild Echinochloa species and broad-leaved annual weeds which include a great variety of paddy field weeds capable of growing in very high density, robbing the paddy rice plant of fertilizer nutrients throughout the whole period of growth, causing ill ventilation and struggling for space against the paddy rice plant. The substituted phenyl (thiono)carbamates of general formula (I) produce remarkable eradicative effects against the above-mentioned weeds during the period from their germination to the two-leaf stage. Against cultivated land weeds, they are most effective at the time of germination.

Among the substituted phenyl (thiono)carbamates of general formula (I), especially preferred from the viewpoint of herbicical activity against various weeds are compounds of the general formula (I-a)

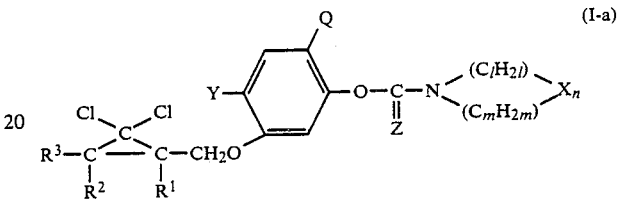

(I-a)

wherein X, l, m, n, Y, $R^1$, $R^2$, $R^3$ and Z are as defined for general formula (I), Q is a hydrogen or halogen atom and the heterocycle comprising the nitrogen atom, the two alkylene chains and X is 5- or 6-membered.

The following compounds, for instance, are representative of the substituted phenyl (thiono)carbamates of general formula (I):

| Structural formula | Melting point (mp) or refractive index at t °C. ($n_D^t$) |
|---|---|
| Compound (1) 4-Chloro-3-[(2,2-dichlorocyclopropyl)methoxy]-phenyl 1-pyrrolidinecarboxylate | mp = 72–74° C. |
| Compound (2) 4-Chloro-3-[(2,2-dichloro-1-methylcyclopropyl)-methoxy]phenyl 1-pyrrolidinecarboxylate | mp = 112–115.5° C. |
| Compound (3) 4-Chloro-3-[(2,2-dichloro-3,3-dimethylcyclopropyl)-methoxy]phenyl 1-pyrrolidinecarboxylate | mp = 75–86.5° C. |
| Compound (4) 4-Chloro-3-[(2,2-dichloro-cis-3-methoxycyclopropyl)-methoxy]phenyl 1-pyrrolidinecarboxylate | $n_D^{22}$ = 1.5515 |

-continued

| | Structural formula | Melting point (mp) or refractive index at t °C. ($n_D^t$) |
|---|---|---|
| Compound (5) | 4-Chloro-3-[(2,2-dichloro-trans-3-methylcyclopropyl)methoxy]phenyl 1-pyrrolidinecarboxylate | $n_D^{22}$ = 1.5523 |
| Compound (6) | 4-Chloro-3-[(2,2-dichloro-3-phenylcyclopropyl)methoxy]phenyl 1-pyrrolidinecarboxylate | $n_D^{22}$ = 1.5812 |
| Compound (7) | 4-Chloro-3-[(2,2-dichlorocyclopropyl)methoxy]phenyl 3-thiazolidinecarboxylate | mp = 74–79.5° C. |
| Compound (8) | 4-Chloro-3-[(2,2-dichlorocyclopropyl)methoxy]phenyl 1-(2-methylpiperidine)carboxylate | mp = 90–106° C. |
| Compound (9) | 4-Chloro-3-[(2,2-dichlorocyclopropyl)methoxy]phenyl 1-piperidinecarboxylate | mp = 96–100° C. |
| Compound (10) | 4-Chloro-3-[(2,2-dichlorocyclopropyl)methoxy]phenyl 1-perhydroazepinecarboxylate | mp = 89–97° C. |
| Compound (11) | 4-Chloro-3-[(2,2-dichlorocyclopropyl)methoxy]phenyl 4-morpholinecarboxylate | mp = 104–107° C. |
| Compound (12) | 4-Chloro-3-[(2,2-dichlorocyclopropyl)methoxy]phenyl 1-(3-pyrroline)carboxylate | $n_D^{22}$ = 1.5663 |

|  | Structural formula | Melting point (mp) or refractive index at t °C. ($n_D^t$) |
|---|---|---|
| Compound (13) | 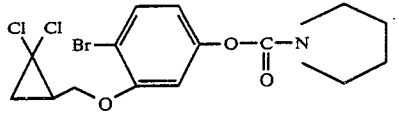<br>4-Bromo-3-[(2,2-dichlorocyclopropyl)methoxy]-phenyl 1-pyrrolidinecarboxylate | mp = 73.5–75° C. |
| Compound (14) | 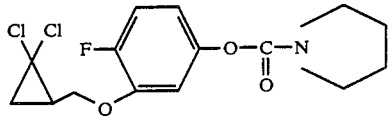<br>4-Fluoro-3-[(2,2-dichlorocyclopropyl)methoxy]-phenyl 1-pyrrolidinecarboxylate | $n_D^{22}$ = 1.5510 |
| Compound (15) | 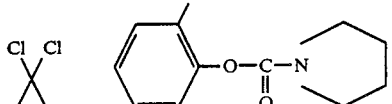<br>2-Chloro-5-[(2,2-dichlorocyclopropyl)methoxy]-phenyl 1-pyrrolidinecarboxylate | $n_D^{22}$ = 1.5571 |
| Compound (16) | 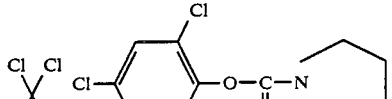<br>2,4-Dichloro-5-[(2,2-dichlorocyclopropyl)-methoxy]phenyl 1-pyrrolidinecarboxylate | $n_D^{27}$ = 1.5640 |
| Compound (17) | <br>3-Chloro-4-[(2,2-dichlorocyclopropyl)methoxy]-phenyl 1-pyrrolidinecarboxylate | $n_D^{22}$ = 1.5578 |
| Compound (18) | 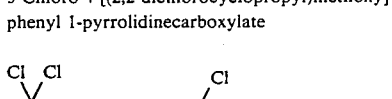<br>2-Chloro-4-[(2,2-dichlorocyclopropyl)methoxy]-phenyl 1-pyrrolidinecarboxylate | $n_D^{27}$ = 1.5557 |
| Compound (19) | 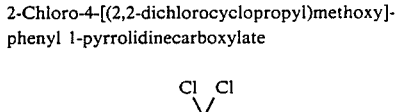<br>4-Chloro-2-[(2,2-dichlorocyclopropyl)methoxy]-phenyl 1-pyrrolidinecarboxylate | mp = 106–111° C. |

|  | Structural formula | Melting point (mp) or refractive index at t °C. ($n_D^t$) |
|---|---|---|
| Compound (20) | 2,4-Dichloro-5-[(2,2-dibromo-1-methylcyclopropyl)-methoxy]phenyl 1-pyrrolidinecarboxylate | mp = 139.8–141.8° C. |
| Compound (21) | O—[4-Chloro-3-[(2,2-dichlorocyclopropyl)-methoxy]phenyl] 1-pyrrolidinecarboxybothioate | mp = 84–90° C. |
| Compound (22) | O—[4-Chloro-3-[(2,2-dichloro-1-methyl-cyclopropyl)methoxy]phenyl] 1-pyrrolidine-carbothioate | mp = 89–98° C. |
| Compound (23) | O—[4-Chloro-3-[(2,2-dichloro-3,3-dimethylcyclo-propyl)methoxy]phenyl] 1-pyrrolidinecarbothioate | $n_D^{20}$ = 1.5849 |
| Compound (24) | O—[4-Chloro-3-[(2,2-dichloro-cis-3-methylcyclo-propyl)methoxy]phenyl] 1-pyrrolidinecarbothioate | $n_D^{20}$ = 1.5778 |
| Compound (25) | O—[4-Chloro-3-[(2,2-dichloro-trans-3-methylcyclopropyl)methoxy]phenyl] 1-pyrrolidinecarbothioate | $n_D^{20}$ = 1.5773 |
| Compound (26) | O—[4-Chloro-3-[(2,2-dichloro-3-phenylcyclopropyl)-methoxy]phenyl] 1-pyrrolidinecarbothioate | $n_D^{20}$ = 1.6140 |
| Compound (27) | O—[4-Chloro-3-[(2,2-dichlorocyclopropyl)methoxy]-phenyl] 3-thiazolidinecarbothioate | mp = 84–93.5° C. |

-continued

| Structural formula | Melting point (mp) or refractive index at t °C. ($n_D^t$) |
|---|---|
| Compound (28) 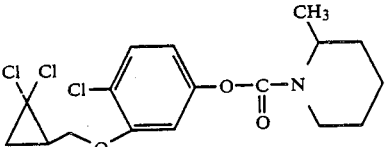 O—[4-Chloro-3-[(2,2-dichlorocyclopropyl)-methoxy]phenyl] 1-(2-methylpiperidine)-carbothioate | mp = 94–114° C. |
| Compound (29) 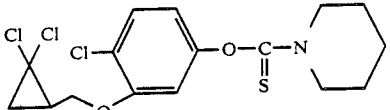 O—[4-Chloro-3-[(2,2-dichlorocyclopropyl)-methoxy]phenyl] 1-piperidinecarbothioate | mp = 61–75° C. |
| Compound (30) 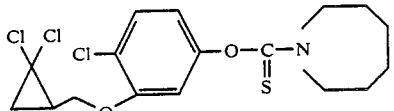 O—[4-Chloro-[(2,2-dichlorocyclopropyl)-methoxy]phenyl] 1-perhydroazepinecarbothioate | $n_D^{20}$ = 1.5918 |
| Compound (31) 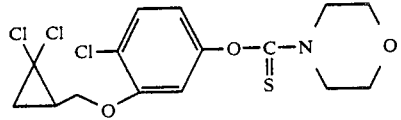 O—[4-Chloro-3-[(2,2-dichlorocyclopropyl)-methoxy]phenyl] 4-morpholinecarbothioate | mp = 130–132° C. |
| Compound (32) 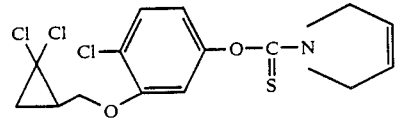 O—[4-Chloro-3-[(2,2-dichlorocyclopropyl)-methoxy]phenyl] 1-(3-pyrroline)carbothioate | mp = 84–89.5° C. |
| Compound (33) 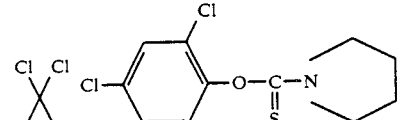 O—[2,4-Dichloro-5-[(2,2-dichlorocyclopropyl)-methoxy]phenyl] 1-pyrrolidinecarbothioate | mp = 68–85° C. |
| Compound (34) 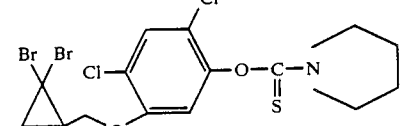 O—[2,4-Dichloro-5[(2,2-dibromo-1-methylcyclopropyl)-methoxy]phenyl] 1-pyrrolidinecarbothioate | mp = 97.4–99.7° C. |

The substituted phenyl (thiono)carbamates of general formula (I) can easily be produced by the following methods (i) to (iii), for instance:

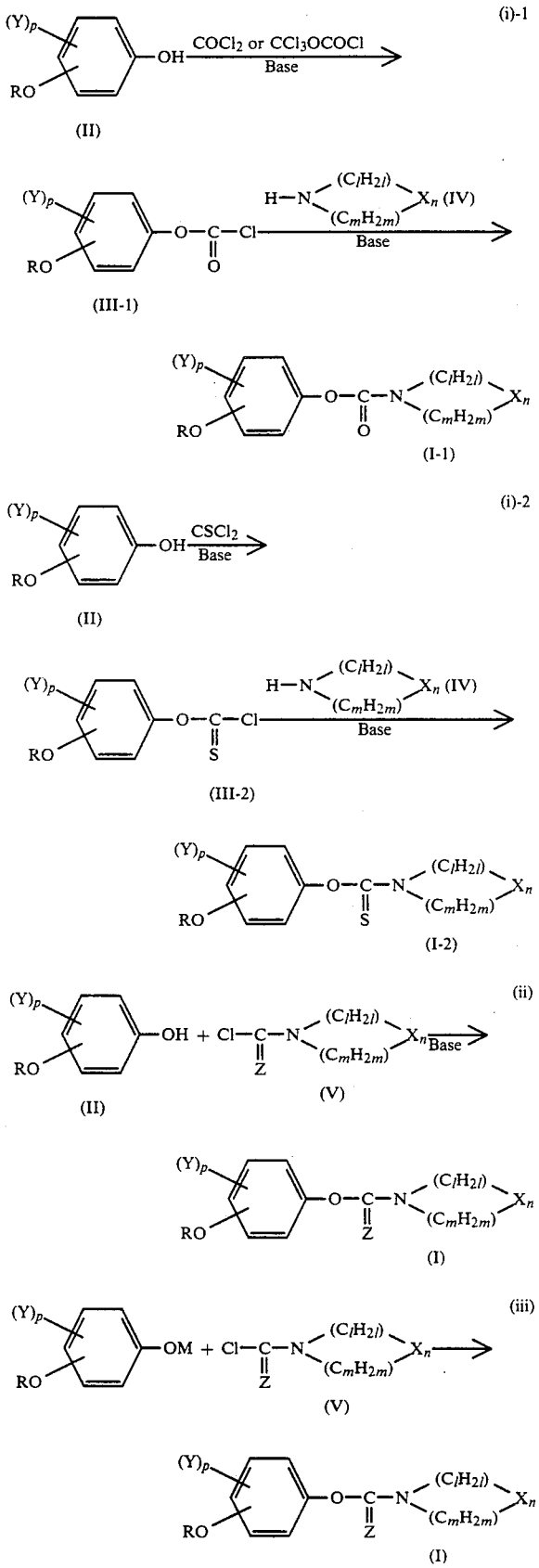

In the above formulas, X, l, m, n, Y, p and Z are as defined for general formula (I), R is the group $$R^3-\underset{R^2}{\underset{|}{C}}-\underset{}{\overset{R^4}{\underset{}{\overset{|}{C}}}\underset{R^5}{\overset{|}{}}}-\underset{R^1}{\underset{|}{C}}-CH_2-$$

in which $R^1$, $R^2$, $R^3$, $R^4$ and $R^5$ are as defined for general formula (I), and M is an alkali metal atom.

In carrying out method (i)-1, a compound of general formula (II) is reacted with phosgene or trichloromethyl chloroformate in the presence of a base and the resulting compound of general formula (III-1) is then reacted with a cyclic amine of general formula (IV) in the presence of a base. In carrying out method (i)-2, a compound of general formula (II) is reacted with thiophosgene in the presence of a base and the resulting compound of general formula (III-2) is then reacted with a cyclic amine of general formula (IV) in the presence of a base. In these methods, said base is, for example, an aliphatic tertiary amine (e.g. trimethylamine, triethylamine), an aromatic tertiary amine (e.g. pyridine, picoline, quinoline), a tertiary aniline (e.g. dimethylaniline, diethylaniline) or an inorganic base (e.g. sodium hydroxide, potassium hydroxide, sodium carbonate, potassium carbonate). In each condensation reaction, the base is used in an amount of at least equivalent to the amount of the starting compound of general formula (II) or (III-1) or (III-2), preferably in an amount of 1 to 3 equivalents. In the condensation reaction between the compound of general formula (III-1) or (III-2) and the cyclic amine of general formula (IV), the latter may be used in an amount of two or more equivalents per mole of the former so that the excess amine can serve as the base. These condensation reactions are preferably carried out in a solvent. Usable solvents are, for example, such ethers as diethyl ether, tetrahydrofuran, dioxane and ethylene glycol dimethyl ether; such hydrocarbons as n-hexane and benzene; such aliphatic ketones as acetone; such chlorine-containing hydrocarbons as methylene chloride, chloroform and carbon tetrachloride; such aliphatic carboxylic acid esters as methyl acetate and ethyl acetate; dimethyl sulfoxide; and N,N-dimethylformamide. These condensation reactions are generally carried out at $-50°$ C. to 200° C., preferably at $-10°$ C. to 100° C.

Method (ii) shown above can be carried out under the same conditions as for method (i)-1 or (i)-2 except that the cyclic amine of general formula (IV), which is the starting material for methods (i)-1 and (i)-2, cannot be used as the base. Method (iii) is carried out by reacting the compound of general formula (VI) with the compound of general formula (V), preferably in a solvent, at a temperature of $-50°$ C. to 200° C., preferably 0° C. to 100° C. Any of the solvents mentioned above for methods (i)-1 and (i)-2 can be used as the solvent.

In practical application, the compounds of the invention may be used alone by themselves without adding any other ingredients. For ease in use as herbicides, however, it is a general practice to formulate them with a carrier and apply the resulting formulations, if necessary after adequate dilution. In formulating, the compounds of the invention are mixed in accordance with a conventional pesticide formulation technology with a liquid or solid carrier, optionally using a surfactant, which serves as an emulsifying and/or dispersing and-/or foaming agent, to give desired formulations in the form of wettable powders, emulsifiable concentrates, granular formulations, etc.

Suitable liquid carriers include, among others, aromatic hydrocarbons (e.g. xylene, toluene, benzene, alkylnaphthalene), chlorinated aromatic or aliphatic hydrocarbons (e.g. chlorobenzene, chloroethylene, methylene chloride), aliphatic or alicyclic hydrocarbons (e.g. cyclohexane, paraffin such as mineral oil fraction), alcohols (e.g. butanol, ethylene glycol and ethers or esters thereof) and ketones (e.g. acetone, methyl ethyl ketone, methyl isobutyl ketone, cyclohexanone, isophorone).

Preferably solid carriers are pulverized natural minerals, such as kaolin, clay, talc, bentonite, sericite-containing kaolin (available under the trademark "Zeklite", for instance), chalk, quartz, attapulgite, montmorillonite and diatomaceous earth; and pulverized synthetic minerals, such as alumina, silicates and white carbon.

Preferable examples of the emulsifier and foaming agent are nonionic and anionic emulsifiers, such as polyoxyethylene aliphatic carboxylic acid esters, polyoxyethylene aliphatic alcohol ethers (e.g. alkylaryl polyglycol ether), alkyl-sulfonates, alkylsulfates, arylsulfonates and albumin hydrolyzate. Preferable examples of the dispersing agent are ligninsulfite waste and methylcellulose.

In preparing the herbicidal compositions of the invention, two or more of the substituted phenyl (thiono)carbamates of general formula (I) may be used combinedly so that the compositions may have excellent herbicidal activity. Furthermore, the compositions may contain fertilizers, insecticides, fungicides, other herbicides and/or plant growth regulators, which are applicable in the same field of use. In particular, it is also preferable that the substituted phenyl thionocarbamates of general formula (I-2) are applied in combination with α-(β-naphthoxy)propionic acid derivatives, such as α-(β-naphthoxy)propionanilide [hereinafter referred to as Compound (a)], N-(2-chlorophenyl)-α-(β-naphthoxy)-propionamide [Compound (b)] and N-(2-fluorophenyl)-α-(β-naphthoxy)propionamide [Compound (c)], or pyrazole derivatives, such as 4-(2,4-dichlorobenzoyl)-1,3-dimethylpyrazol-5-yl p-toluenesulfonate [Compound (d)] and 4-(2,4-dichlorobenzoyl)-1,3-dimethyl-5-phenacyloxypyrazole [Compound (e)]. Such combinations can effectively control various annual and perennial weeds at low doses. In particular, the compositions can control Cyperus serotinus ROTTB., Sagittaria pygmaea MIQ. (arrowhead) and similar perennial weeds in very small doses as compared with the case in which the component herbicides each is applied alone, without producing any phytotoxic effect on useful crop plants such as paddy rice plant. The ratio of the substituted phenyl thionocarbamates of general formula (I-2) to the above-mentioned α-(β-naphthoxy)propionic acid derivative or pyrazole derivative is suitably in the range of 1:0.02 to 1:50, especially desirably in the range of 1:0.1 to 1:20.

The formulated herbicidal compositions should contain at least $1 \times 10^{-3}$ percent by weight, preferably 0.01–95 percent by weight, more preferably 0.1–80 percent by weight, of the active ingredients, namely either the compounds of the invention or combinations of the compounds of the invention and other herbicidal compounds.

The compounds of the invention may be applied either in various formulation forms such as mentioned above or in application forms obtainable by further processing such formulation forms. The application forms may contain the compounds of the invention in an amount adequately selected from within a very wide range from $1 \times 10^{-5}$ to 100 percent by weight, preferably from $1 \times 10^{-3}$ to 30 percent by weight. When the compounds of the invention are used in combination with other herbicidal compounds, the total content of the active ingredients in the application forms may be selected within the same range as mentioned above, namely $1 \times 10^{-5}$ to 100 percent by weight.

The herbicidal compositions of the invention can be applied by any conventional method suited for the application form chosen. The compounds of the invention are used in an amount of at least 1 g per 10 ares, preferably 2.5 to 2,000 g per 10 ares, more preferably 10 to 1,000 g per 10 ares.

Since the herbicides of the invention are remarkably active against weeds during the period from their emergence to the two-leaf stage, they are preferably applied within this period.

The following examples of the synthesis of the compounds of the invention, formulation examples and utility examples further illustrate the invention but are by no means limitative of the invention. In the formulation examples, "part(s)" means "part(s) by weight". The compounds referred to by numbers respectively correspond to the previously mentioned substituted phenyl (thiono)carbamates (1) to (34), represented by general formula (I).

SYNTHESIS EXAMPLE 1

Synthesis of
4-chloro-3-[(2,2-dichlorocyclopropyl)methoxy]phenol
and of
2-chloro-5-[(2,2-dichlorocyclopropyl)methoxy]phenol

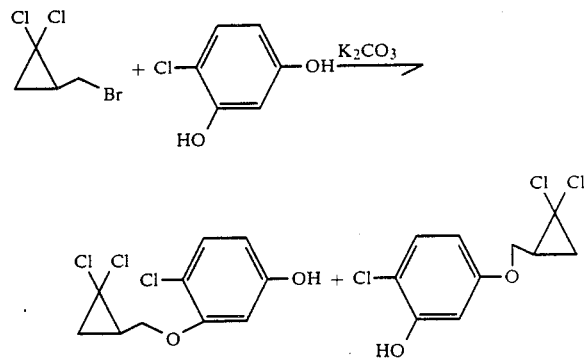

In 700 ml of N,N-dimethylformamide, there was dissolved 181 g of 4-chlororesorcinol. To the solution, there were added 283 g of (2,2-dichlorocyclopropyl)-methyl bromide, 207 g of anhydrous potassium carbonate and 4 g of sodium iodide. The mixture was stirred at 90° C. for 15 hours, then poured into ice water and extracted with diethyl ether. The ether layer was washed with water and dried over anhydrous magnesium sulfate, and the solvent was then distilled off. The oily residue was subjected to preparatory high-speed liquid chromatography to give 93 g of 4-chloro-3-[(2,2-dichlorocyclopropyl)methoxy]phenol and 5 g of 2-chloro-5-[(2,2-dichlorocyclopropyl)methoxy]phenol.

Synthesis of 4-chloro-3-[(2,2-dichlorocyclopropyl)methoxy]phenyl 1-pyrrolidinecarboxylate [Compound (1)]

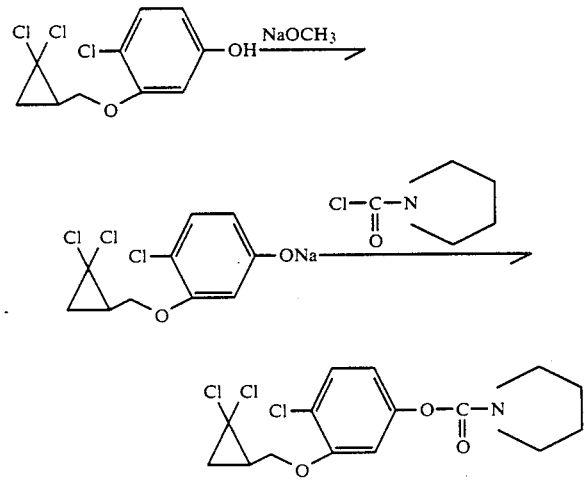

80 g of 4-chloro-3-[(2,2-dichlorocyclopropyl)methoxy]phenol was dissolved in 200 ml of methanol, then 58 g of a 28% solution of sodium methylate in methanol was added to the solution, and the methanol was then distilled off completely. The thus-prepared sodium salt of 4-chloro-3-[(2,2-dichlorocyclopropyl)methoxy]phenol was dissolved in 500 ml of N,N-dimethylformamide. To this solution was added 56 g of 1-pyrrolidinecarbonyl chloride. The mixture was stirred at 60° C. for 10 hours, then poured into ice water and extracted with diethyl ether. The ether was distilled off from the ether layer. The residue was purified by silica gel column chromatography to give 79 g of 4-chloro-3-[(2,2-dichlorocyclopropyl)methoxy]phenyl 1-pyrrolidinecarboxylate [Compound (1)]. The product had the melting point of 72°–74° C.

Following the above procedure, there were prepared Compounds (2) to (6) and (13) to (20). Each compound had the melting point or refractive index as mentioned above.

SYNTHESIS EXAMPLE 2

Synthesis of 4-chloro-3-[(2,2-dichlorocyclopropyl)methoxy]phenyl 3-thiazolidinecarboxylate [Compound (7)]

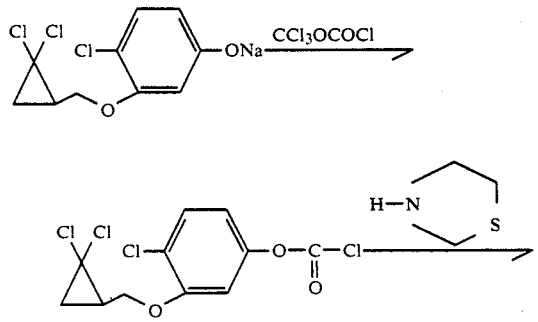

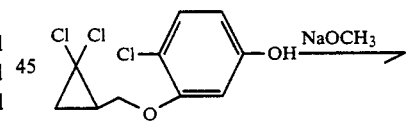

The sodium salt of 4-chloro-3-[(2,2-dichlorocyclopropyl)methoxy]phenol as prepared from 20 g of 4-chloro-3-[(2,2-dichlorocyclopropyl)methoxy]phenol and 16 g of a 28% methanol solution of sodium methylate was dissolved in 300 ml of water and the solution was added dropwise to a solution of 5 ml of trichloromethyl chloroformate in 100 ml of chloroform while maintaining the reaction temperature at 10° C. or below. The reaction mixture was allowed to stand for phase separation. The chloroform layer was dried over anhydrous magnesium sulfate and the solvent was then distilled off. There was obtained 22.5 g of 4-chloro-3-[(2,2-dichlorocyclopropyl)methoxy]phenyl chloroformate.

1.00 g of 4-chloro-3-[(2,2-dichlorocyclopropyl)methoxy]phenyl chloroformate was dissolved in 20 ml of diethyl ether and, to the solution, there were added 0.32 g of thiazolidine and 0.37 g of triethylamine. The mixture was stirred at 0° to −5° C. for an hour and then washed with water. The ether was distilled off from the ether layer and the oily residue was purified by silica gel column chromatography to give 1.02 g of 4-chloro-3-[(2,2-dichlorocyclopropyl)methoxy]phenyl 3-thiazolidinecarboxylate [Compound (7)], which had the melting point of 74°–79.5° C.

Following the above procedure, there were obtained Compounds (8) to (12). Each product had the melting point or refractive index as mentioned hereinbefore.

SYNTHESIS EXAMPLE 3

Synthesis of O-[4-chloro-3-[(2,2-dichlorocyclopropyl)methoxy]phenyl] 1-pyrrolidinecarbothioate [Compound (21)]

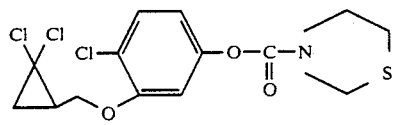

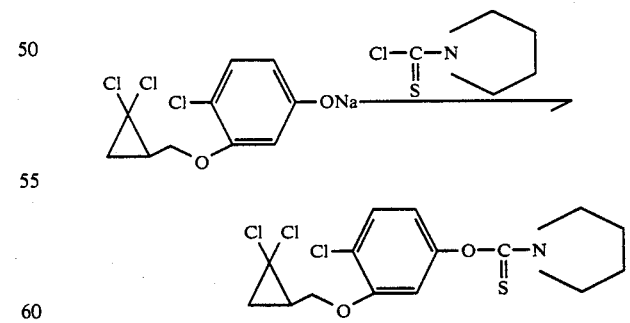

80 g of 4-chloro-3-[(2,2-dichlorocyclopropyl)methoxy]phenol was dissolved in 200 ml of methanol, and 58 g of a 28% solution of sodium methylate in methanol was added to the solution. The methanol was then distilled off completely. The thus-prepared sodium salt of 4-chloro-3-[(2,2-dichlorocyclopropyl)methoxy]phenol was dissolved in 500 ml of N,N-dimethylformamide and, to this solution, 56 g of 1-pyrrolidinethiocarbonyl chloride was added. The mixture was stirred at 60° C. for 10 hours, then poured into ice water and extracted with diethyl ether. The solvent was distilled off from the ether layer and the residue was purified by silica gel column chromatography to give 47 g of O-[4-chloro-3-[(2,2-dichlorocyclopropyl)methoxy]phenyl] 1-pyrrolidinecarbothioate [Compound (21)]. Melting point of the product: 84°–90° C.

Following the above procedure, there were obtained Compounds (22) to (26), (33) and (34). Each compound had the melting point or refractive index as described hereinbefore.

SYNTHESIS EXAMPLE 4

Synthesis of O-[4-chloro-3-](2,2-dichlorocyclopropyl)methoxy]phenyl] 3-thiazolidinecarbothioate [Compound (27)]

The sodium salt of 4-chloro-3-[(2,2-dichlorocyclopropyl)methoxy]phenol as prepared from 9.7 g of 4-chloro-3-[(2,2-dichlorocyclopropyl)methoxy]phenol and 7 g of a 28% solution of sodium methylate in methanol was dissolved in 300 ml of water and the solution was added dropwise to a solution of 3.2 ml of thiophosgene in 100 ml of chloroform while maintaining the reaction temperature at 10° C. or below. The reaction mixture was allowed to stand for phase separation, the chloroform layer was dried over anhydrous magnesium sulfate, and the solvent was distilled off to give 11.2 g of O-[4-chloro-3-[(2,2-dichlorocyclopropyl)methoxy]-phenyl]chlorothioformate.

The O-[4-chloro-3-[(2,2-dichlorocyclopropyl)methoxy]phenyl]chlorothioformate (1.00 g) was dissolved in 20 ml of diethyl ether and, to the solution, there were added 0.31 g of thiazolidine and 0.35 g of triethylamine. The mixture was stirred at 0° C. to −5° C. for an hour and then washed with water. The ether was distilled off from the ether layer. The thus-obtained oily substance was purified by silica gel column chromatography to give 1.11 g of O-[4-chloro-3-[(2,2-dichlorocyclopropyl)methoxy]phenyl] 3-thiazolidinecarbothioate [Compound (27)]. Metling point of the product: 84°–93.5° C.

Compounds (28) to (32) were also prepared by the above procedure. Each compound had the melting point or refractive index as described hereinbefore.

FORMULATION EXAMPLE 1

Emulsifiable Concentrate

Thirty (30) parts of each of Compounds (1) to (34) was prepared, and thereto were added 60 parts of a 1:1 mixture of xylene and isophorone and 10 parts of nonionic surfactant (Sorpol 800A: a mixture of an alkylaryl ether of polyoxyethylene glycol, a polyoxyethylene sorbitan alkylate, a polyoxyethylene ester of a fatty acid and an alkylarylsulfonate, manufactured by Toho Chemical Co., Ltd.). Each mixture was stirred well to give 100 parts of an emulsifiable concentrate.

FORMULATION EXAMPLE 2

Wettable Powder

A wettable powder carrier (100 parts) was prepared by grinding and mixing 97 parts of sericite containing kaolin (Zeklite), 1.5 parts of anionic surfactant (Neoperex: sodium alkylbenzenesulfonate, manufactured by Kao-Atlas Co., Ltd.) and 1.5 parts of nonionic surfactant (Sorpol 800A as mentioned above).

Ten (10) parts of each of Compounds (1) to (34) was perpared and thereto was added 90 parts of the above wettable powder carrier. The mixture was ground and mixed to give 100 parts of a wettable powder.

FORMULATION EXAMPLE 3

Wettable Powder

Fifty (50) parts of each of Compounds (21) to (34) was prepared and mixed well with 5 parts of nonionic surfactant (Sorpol 800A as mentioned above). Further addition of 45 parts of a 1:1 mixture of talc and bentonite followed by stirring and mixing in a triturator gave 100 parts of a wettable powder.

FORMULATION EXAMPLE 4

Granular Composition

Water (10 parts) was added to 10 parts of each of Compounds (1) to (34), 80 parts of a 1:3 diluent mixture of talc and bentonite, 5 parts of white carbon and 5 parts of nonionic surfactant (Sorpol 800A as mentioned above). The mixture was kneaded, the resulting paste was extruded through sieve meshes 0.7 mm in diameter, and the extrudate was dried and cut to 0.5 to 1 mm long pieces to give 100 parts of a granular composition.

FORMULATION EXAMPLE 5

Emulsifiable Concentrate

Fifteen (15) parts of each of Compounds (21) to (34) was prepared and thereto were added 15 parts of Compound (a), 60 parts of a 1:1 mixture of xylene and isophorone and 10 parts of nonionic surfactant (Sorpol 800A as mentioned above). Adequate stirring and mixing gave 100 parts of an emulsifiable concentrate.

Using 15 parts of Compound (d) in place of 15 parts of Compound (a) and following the above procedure, there was prepared 100 parts of an emulsifiable concentrate containing any of Compounds (21) to (34) and Compound (d).

FORMULATION EXAMPLE 6

Wettable Powder

Twenty (20) parts of each of Compounds (21) to (34) was prepared and thereto were added 20 parts of Compound (b), 20 parts of white carbon, 5 parts of sodium ligninsulfonate, 2 parts of sodium dodecylbenzenesulfonate and 33 parts of diatomaceous earth. Adequate grinding and mixing gave 100 parts of a wettable powder.

Using 20 parts of Compound (e) in place of 20 parts of Compound (b) and following the above procedure, there was prepared 100 parts of a wettable powder containing any of Compounds (21) to (34) and Compound (e).

FORMULATION EXAMPLE 7

Granular Composition

Four (4) parts of each of Compounds (21) to (34) was prepared and thereto were added 6 parts of Compound (a), 80 parts of a 1:3 diluent mixture of talc and bentonite, 5 parts of white carbon and 5 parts of nonionic surfactant (Sorpol 800A as mentioned above). After mixing, 10 parts of water was added, the resulting paste was extruded through sieve meshes 0.7 mm in diameter, and the extrudate was dried and cut to 1 to 2 mm long pieces to give 100 parts of a granular composition.

Using 6 parts of Compound (d) in place of 6 parts of Compound (a) and following the above procedure, there was prepared a paste. The paste was extruded through sieve meshes 0.7 mm in diameter, and the extrudate was dried and cut to 0.5 to 1 mm long pieces to give 100 parts of a granular composition.

UTILITY EXAMPLE 1

Submerged Soil Treatment

Sieved paddy field soil was placed in a porcelain pot 9 cm in diameter, water was added, and the soil was plowed and sowed with barnyard grass (*Echinochloa crus-galli*), monochoria (*Monochoria vaginalis*), toothcup (*Rotala indica*) and umbrella plant (*Cyperus difformis*). Then two rice seedlings (*Oryza sativa* L., Nipponbare strain) at the two-leaf stage were put in a bundle on the surface of the soil in the pot and other two rice seedlings at the same stage were transplanted in a bundle to the soil in the pot to the depth of 1 cm. The pot was filled with water to the height of 2 cm over the soil surface. A wettable powder containing the test compound was prepared by the procedure of Formulation Example 2 and diluted with water to a prescribed concentration and the resulting preparation was applied onto the water surface one day after the transplantation of the rice seedlings. The herbicidal effect on the weeds and injury to the paddy rice plant were evaluated 21 days after the application according to the criteria shown below. The results obtained are summarized below in Table 1.

Criteria for evaluation of herbicidal effects:

Inhibition of growth of weeds or withering of weeds as compared with the untreated control 5: 80% to 100%
4: Not less than 60% but less than 80%
3: Not less than 40% but less than 60%
2: Not less than 20% but less than 40%
1: Less than 20%
0: 0%

Criteria for evaluation of injury to paddy rice plant:

Inhibition of growth of paddy rice plant as compared with the untreated control

5: 80% to 100%
4: Not less than 60% but less than 80%
3: Not less than 40% but less than 60%
2: Not less than 20% but less than 40%
1: Less than 20%
0: 0%

Browning of leaf sheath portion

+++: Very high degree
++: Medium degree
+: Low degree
±: Slight degree
—: No browning

TABLE 1

| Test compound | Amount of compound (g/10a) | Herbicidal effect | | | | Injury to the paddy rice plant | | | |
|---|---|---|---|---|---|---|---|---|---|
| | | | | | | Put seedlings | | Transplanted seedlings | |
| | | Barnyard grass | Monochoria | Toothcup | Umbrella plant | Inhibition of growth | Browning of leaf sheath | Inhibition of growth | Browning of leaf sheath |
| Compound (1) | 6.25 | 4 | 1.5 | 4.5 | 4.5 | 0 | — | 0 | — |
| | 12.5 | 5 | 4.5 | 5 | 5 | 0 | — | 0 | — |
| | 25 | 5 | 5 | 5 | 5 | 0 | — | 0 | — |
| | 50 | 5 | 5 | 5 | 5 | 0 | — | 0 | ± |
| | 100 | 5 | 5 | 5 | 5 | 0 | ± | 0 | ± |
| Compound (2) | 6.25 | 4.5 | 5 | 4.5 | 4.5 | 0 | — | 0 | — |
| | 12.5 | 4.5 | 4 | 5 | 5 | 0 | — | 0 | — |
| | 25 | 5 | 5 | 5 | 5 | 0 | — | 0 | — |
| | 50 | 5 | 5 | 5 | 5 | 0 | — | 0 | — |
| | 100 | 5 | 5 | 5 | 5 | 0 | — | 0 | — |
| Compound (3) | 6.25 | 4 | 4 | 1.5 | 2 | 0 | — | 0 | — |
| | 12.5 | 4 | 4 | 4.5 | 4.5 | 0 | — | 0 | — |
| | 25 | 4.5 | 5 | 4.5 | 5 | 0 | — | 0 | — |
| | 50 | 5 | 5 | 4.5 | 5 | 0 | — | 0 | ± |
| | 100 | 5 | 5 | 5 | 5 | 0 | — | 0 | ± |
| Compound (4) | 6.25 | 3.5 | 4.5 | 1.5 | 2 | 0 | — | 0 | — |
| | 12.5 | 4.5 | 5 | 4.5 | 4.5 | 0 | — | 0 | — |
| | 25 | 5 | 5 | 5 | 5 | 0 | — | 0 | — |
| | 50 | 5 | 5 | 5 | 5 | 0 | — | 0 | — |
| | 100 | 5 | 5 | 5 | 5 | 0 | ± | 0 | ± |
| Compound (5) | 6.25 | 3.5 | 2 | 1 | 2 | 0 | — | 0 | — |
| | 12.5 | 4 | 2.5 | 4.5 | 4.5 | 0 | — | 0 | — |
| | 25 | 4.5 | 3 | 5 | 5 | 0 | — | 0 | — |
| | 50 | 5 | 5 | 5 | 5 | 0 | — | 0 | — |
| | 100 | 5 | 5 | 5 | 5 | 0 | — | 0 | ± |
| Compound (16) | 6.25 | 3 | 4 | 3 | 2 | 0 | — | 0 | — |
| | 12.5 | 4.5 | 4.5 | 4 | 4.5 | 0 | — | 0 | — |
| | 25 | 5 | 5 | 5 | 5 | 0 | — | 0 | — |
| | 50 | 5 | 5 | 5 | 5 | 0 | — | 0 | — |
| | 100 | 5 | 5 | 5 | 5 | 0 | — | 0 | ± |
| Control compound (A) (*1) | 6.25 | 0 | 1 | 0 | 0 | 0 | — | 0 | — |
| | 12.5 | 1 | 1.5 | 1 | 0 | 0 | — | 0 | — |
| | 25 | 2.5 | 3 | 1.5 | 1 | 0 | — | 0 | — |
| | 50 | 3 | 4 | 2 | 3 | 0 | — | 0 | — |
| | 100 | 3 | 4.5 | 3 | 3.5 | 0 | — | 0 | — |
| Control compound (B) (*2) | 6.25 | 0 | 0 | 0 | 0 | 0 | — | 0 | — |
| | 12.5 | 0 | 0 | 0 | 0 | 0 | — | 0 | — |
| | 25 | 1 | 1 | 1.5 | 0.5 | 0 | — | 0 | — |
| | 50 | 3 | 1.5 | 1.5 | 2 | 0 | — | 0 | — |
| | 100 | 3.5 | 2.5 | 2 | 3 | 0 | — | 0 | — |

TABLE 1-continued

| Test compound | Amount of compound (g/10a) | Herbicidal effect | | | | Injury to the paddy rice plant | | | |
|---|---|---|---|---|---|---|---|---|---|
| | | | | | | Put seedlings | | Transplanted seedlings | |
| | | Barnyard grass | Monochoria | Toothcup | Umbrella plant | Inhibition of growth | Browning of leaf sheath | Inhibition of growth | Browning of leaf sheath |
| Control compound (commercial product) | 6.25 | 2 | 5 | 3 | 2 | 0 | — | 0 | — |
| | 12.5 | 3 | 5 | 4 | 4.5 | 0 | — | 0 | — |
| | 25 | 4.5 | 5 | 4.5 | 5 | 0 | — | 0 | ± |
| | 50 | 4.5 | 5 | 5 | 5 | 0 | ± | 0 | + |
| CNP | 100 | 5 | 5 | 5 | 5 | 0 | ± | 0 | + |
| Untreated control | 0 | 0 | 0 | 0 | 0 | 0 | — | 0 | — |

(*1) Control compound (A) has the following formula.

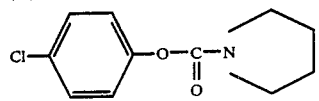

(*2) Control compound (B) has the following formula.

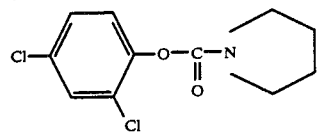

UTILITY EXAMPLE 2

Submerged Soil Treatment

Sieved paddy field soil was placed in a porcelain pot 9 cm in diameter, water was added, and the soil was plowed and sowed with barnyard grass (*Echinochloa crus-galli*), monochoria (*Monochoria vaginalis*), toothcup (*Rotala indica*) and umbrella plant (*Cyperus difformis*). Then two rice seedlings (*Oryza sativa* L, Nipponbare strain) at the two-leaf stage were put in a bundle on the surface of the soil in the pot and other two rice seedlings at the same stage were transplanted in a bundle to the soil in the pot to the depth of 1 cm. The pot was filled with water to the height of 2 cm over the soil surface. A wettable powder containing the test compound was prepared by the procedure of Formulation Example 2 and diluted with water to a prescribed concentration and the resulting preparation was applied onto the water surface one day after the transplantation of the rice seedlings. The herbicidal effect on the weeds and injury to the paddy rice plant were evaluated 21 days after the application according to the criteria shown in Utility Example 1. The results obtained are shown in Table 2.

TABLE 2

| Test compound | Amount of compound (g/10a) | Herbicidal effect | | | | Injury to the paddy rice plant | | | |
|---|---|---|---|---|---|---|---|---|---|
| | | | | | | Put seedlings | | Transplanted seedlings | |
| | | Barnyard grass | Monochoria | Toothcup | Umbrella plant | Inhibition of growth | Browning of leaf sheath | Inhibition of growth | Browning of leaf sheath |
| Compound (9) | 25 | 4 | 2.5 | 4.5 | 4.5 | 0 | — | 0 | — |
| | 50 | 4.5 | 4 | 5 | 4.5 | 0 | — | 0 | — |
| | 100 | 5 | 5 | 5 | 4.5 | 0 | — | 0 | — |
| | 250 | 5 | 5 | 5 | 5 | 0 | — | 0 | — |
| Compound (11) | 25 | 4 | 4.5 | 4.5 | 4.5 | 0 | — | 0 | — |
| | 50 | 4.5 | 5 | 5 | 5 | 0 | — | 0 | — |
| | 100 | 5 | 5 | 5 | 5 | 0 | — | 0 | — |
| | 250 | 5 | 5 | 5 | 5 | 0 | — | 0 | — |
| Compound (13) | 25 | 4 | 3 | 5 | 4.5 | 0 | — | 0 | — |
| | 50 | 5 | 5 | 5 | 4.5 | 0 | — | 0 | — |
| | 100 | 5 | 5 | 5 | 5 | 0 | — | 0 | — |
| | 250 | 5 | 5 | 5 | 5 | 0 | — | 0 | — |
| Compound (14) | 25 | 3.5 | 2.5 | 4.5 | 4.5 | 0 | — | 0 | — |
| | 50 | 5 | 4.5 | 5 | 5 | 0 | — | 0 | — |
| | 100 | 5 | 5 | 5 | 5 | 0 | — | 0 | — |
| | 250 | 5 | 5 | 5 | 5 | 0 | — | 0 | — |
| Untreated control | 0 | 0 | 0 | 0 | 0 | 0 | — | 0 | — |

UTILITY EXAMPLE 3

Submerged Soil Treatment

Sieved paddy field soil was placed in a porcelain pot 9 cm in diameter, water was added, and the soil was plowed and sowed with barnyard grass (*Echinochloa crus-galli*), monochoria (*Monochoria vaginalis*), toothcup (*Rotala indica*) and umbrella plant (*Cyperus difformis*). Then two rice seedlings (*Oryza sativa* L, Nipponbare strain) at the two-leaf stage were put in a bundle on the surface of the soil in the pot and other two rice seedlings at the same stage were transplanted in a bundle to the soil in the pot to the depth of 1 cm. The pot was filled with water to the height of 2 cm over the soil surface. A wettable powder containing the test compound was prepared by the procedure of Formulation Example 2 and diluted with water to a prescribed concentration and the resulting preparation was applied onto the water surface one day after the transplantation of the rice seedlings. The herbicidal effect on the weeds and injury to the paddy rice plant were evaluated 21 days after the application according to the criteria shown in Utility Example 1. The results obtained are shown in Table 3.

Nipponbare strain) at the two-leaf stage were put in a bundle on the surface of the soil in the pot and other two rice seedlings at the same stage were transplanted in a bundle to the soil in the pot to the depth of 1 cm.

TABLE 3

| Test compound | Amount of compound (g/10a) | Herbicidal effect | | | | Injury to the paddy rice plant | | | |
|---|---|---|---|---|---|---|---|---|---|
| | | | | | | Put seedlings | | Transplanted seedlings | |
| | | Barnyard grass | Monochoria | Toothcup | Umbrella plant | Inhibition of growth | Browning of leaf sheath | Inhibition of growth | Browning of leaf sheath |
| Compound (6) | 100 | 4.5 | 4.5 | 5 | 5 | 0 | — | 0 | — |
| | 250 | 4.5 | 5 | 5 | 5 | 0 | — | 0 | ± |
| | 500 | 5 | 5 | 5 | 5 | 0 | — | 0 | ± |
| | 1000 | 5 | 5 | 5 | 5 | 0.5 | ± | 0 | + |
| Compound (7) | 100 | 4.5 | 5 | 4.5 | 4 | 0 | — | 0 | — |
| | 250 | 4.5 | 5 | 4.5 | 5 | 0 | — | 0 | — |
| | 500 | 5 | 5 | 5 | 5 | 0 | — | 0 | — |
| | 1000 | 5 | 5 | 5 | 5 | 0 | — | 0 | — |
| Compound (8) | 100 | 2 | 1.5 | 3 | 3 | 0 | — | 0 | — |
| | 250 | 4 | 4.5 | 5 | 4 | 0 | — | 0 | — |
| | 500 | 4 | 5 | 5 | 5 | 0 | — | 0 | — |
| | 1000 | 4 | 5 | 5 | 5 | 0 | ± | 0 | ± |
| Compound (10) | 100 | 2 | 1.5 | 1 | 2 | 0 | — | 0 | — |
| | 250 | 2.5 | 3 | 2 | 3 | 0 | — | 0 | — |
| | 500 | 2 | 5 | 3 | 3 | 0 | — | 0 | — |
| | 1000 | 4 | 5 | 4 | 4 | 0 | — | 0 | — |
| Compound (12) | 100 | 2.5 | 5 | 3 | 2 | 0 | — | 0 | — |
| | 250 | 4.5 | 5 | 4.5 | 5 | 0 | — | 0 | — |
| | 500 | 5 | 5 | 5 | 5 | 0 | — | 0 | — |
| | 1000 | 5 | 5 | 5 | 5 | 0 | — | 0 | — |
| Compound (15) | 100 | 1.5 | 2 | 1.5 | 2 | 0 | — | 0 | — |
| | 250 | 4.5 | 3.5 | 3 | 4 | 0 | — | 0 | — |
| | 500 | 5 | 4.5 | 3.5 | 4.5 | 0 | — | 0 | — |
| | 1000 | 5 | 5 | 4.5 | 5 | 0 | — | 0 | — |
| Compound (17) | 100 | 1.5 | 2 | 1.5 | 3 | 0 | — | 0 | — |
| | 250 | 3 | 2.5 | 3 | 3.5 | 0 | — | 0 | — |
| | 500 | 4 | 4 | 4.5 | 4 | 0 | — | 0 | — |
| | 1000 | 5 | 5 | 5 | 4.5 | 0 | — | 0 | — |
| Compound (18) | 100 | 1.5 | 1 | 2 | 2 | 0 | — | 0 | — |
| | 250 | 2.5 | 3 | 3.5 | 4.5 | 0 | — | 0 | — |
| | 500 | 4 | 4.5 | 5 | 5 | 0 | — | 0 | — |
| | 1000 | 4.5 | 5 | 5 | 5 | 0 | — | 0 | — |
| Compound (19) | 100 | 1 | 1.5 | 1 | 2 | 0 | — | 0 | — |
| | 250 | 3 | 2 | 2.5 | 3.5 | 0 | — | 0 | — |
| | 500 | 4 | 3.5 | 4 | 4.5 | 0 | — | 0 | — |
| | 1000 | 5 | 5 | 5 | 5 | 0 | — | 0 | — |
| Compound (20) | 100 | 1.5 | 3 | 2 | 2 | 0 | — | 0 | — |
| | 250 | 3 | 4 | 4.5 | 4 | 0 | — | 0 | — |
| | 500 | 4.5 | 5 | 5 | 5 | 0 | — | 0 | — |
| | 1000 | 5 | 5 | 5 | 5 | 0 | — | 0 | — |
| Untreated control | 0 | 0 | 0 | 0 | 0 | 0 | — | 0 | — |

UTILITY EXAMPLE 4

Submerged soil treatment

Sieved paddy field soil was placed in a porcelain pot 12 cm in diameter, water was added, and the soil was plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Tubers of *Cyperus serotinus* after forced sprouting were transplanted to the soil and furthermore two rice seedlings (*Oryza sativa* L, The pot was filled with water to the height of 2 cm over the soil surface. A wettable powder containing the test compound was prepared by the procedure of Formulation Example 2 and diluted with water to a prescribed concentration and the resulting preparation was applied onto the water surface two days after the transplantation of the rice seedlings. The herbicidal effect on the weeds and injury to the paddy rice plant were evaluated 20 days after the application according to the criteria shown in Utility Example 1. The results obtained are shown in Table 4.

TABLE 4

| Test compound | Amount of compound (g/10a) | Herbicidal effect | | | | | | Injury to the paddy rice plant | | | |
|---|---|---|---|---|---|---|---|---|---|---|---|
| | | | | | | | | Put seedlings | | Transplanted seedlings | |
| | | Barnyard grass | Monochoria | Toothcup | Umbrella plant | Hardstem bulrush | Cyperus serotinus | Inhibition of growth | Browning of leaf | Inhibition of growth | Browning of leaf |
| Compound (21) | 6.25 | 3 | 3 | 4.5 | 5 | 2 | 1.5 | 0 | — | 0 | — |
| | 12.5 | 5 | 4 | 5 | 5 | 3.5 | 2 | 0 | ± | 0 | — |
| | 25 | 5 | 5 | 5 | 5 | 5 | 3 | 0 | ± | 0 | ± |
| | 50 | 5 | 5 | 5 | 5 | 5 | 4 | 0 | ± | 0 | ± |
| | 100 | 5 | 5 | 5 | 5 | 5 | 4.5 | 0 | + | 0 | + |
| Compound (22) | 6.25 | 2 | 3 | 3.5 | 4 | 1.5 | 1 | 0 | — | 0 | — |
| | 12.5 | 5 | 5 | 5 | 5 | 2 | 2 | 0 | — | 0 | — |

TABLE 4-continued

| Test compound | Amount of compound (g/10a) | Herbicidal effect ||||| Injury to the paddy rice plant ||||
|---|---|---|---|---|---|---|---|---|---|---|
| | | | | | | | Put seedlings || Transplanted seedlings ||
| | | Barnyard grass | Monochoria | Toothcup | Umbrella plant | Hardstem bulrush | Cyperus serotinus | Inhibition of growth | Browning of leaf | Inhibition of growth | Browning of leaf |
| | 25 | 5 | 5 | 5 | 5 | 3.5 | 3 | 0 | ± | 0 | ± |
| | 50 | 5 | 5 | 5 | 5 | 4 | 4 | 0 | ± | 0 | + |
| | 100 | 5 | 5 | 5 | 5 | 5 | 4 | 0 | + | 0 | − |
| Control compound (C) (*3) | 6.25 | 0 | 0 | 0 | 0 | 0 | 0 | 0 | − | 0 | − |
| | 12.5 | 0 | 1 | 1 | 1 | 0 | 0 | 0 | ± | 0 | − |
| | 25 | 1 | 2 | 2 | 2 | 0 | 1 | 0.5 | + | 0 | + |
| | 50 | 1 | 2 | 2 | 2 | 0 | 2 | 1 | +++ | 0.5 | ++ |
| | 100 | 2 | 3 | 4 | 3 | 1 | 2 | 2 | +++ | 1 | +++ |
| Control compound (D) (*4) | 6.25 | 0 | 0 | 0 | 0 | 0 | 0 | 0 | − | 0 | − |
| | 12.5 | 0 | 1 | 1 | 1 | 0 | 0 | 0 | − | 0 | − |
| | 25 | 0 | 2 | 2 | 2 | 0 | 0 | 0 | − | 0 | − |
| | 50 | 0 | 3 | 4 | 3 | 0 | 1 | 0.5 | ± | 0 | − |
| | 100 | 0 | 5 | 5 | 5 | 0 | 2 | 1 | + | 1 | ± |
| Control compound (Commercial product) CNP | 6.25 | 1 | 4.5 | 3.5 | 5 | 0.5 | 0.5 | 0 | ± | 0 | − |
| | 12.5 | 3.5 | 5 | 4.5 | 5 | 0.5 | 1 | 0 | ± | 0 | ± |
| | 25 | 4.5 | 5 | 5 | 5 | 1 | 2 | 0 | ± | 0 | + |
| | 50 | 4.5 | 5 | 5 | 5 | 2 | 3.5 | 0 | + | 0 | ++ |
| | 100 | 5 | 5 | 5 | 5 | 3 | 3.5 | 0 | + | 0 | ++ |
| Untreated control | 0 | 0 | 0 | 0 | 0 | 0 | 0 | 0 | − | 0 | − |

(*3) Control compound (C) has the following formula.

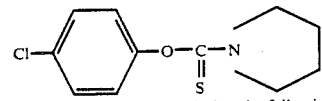

(*4) Control compound (D) has the following formula:

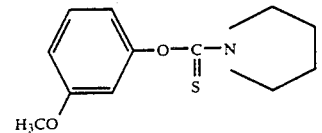

UTILITY EXAMPLE 5

Submerged Soil Treatment

Paddy field soil was placed in a pot 10 cm in diameter and sowed with barnyard grass (*Echinochloa crus-galli*), toothcup (*Rotala indica*), umbrella plant (*Cyperus difformis*) and hardstem bulrush (*Scirpus juncoides*). Furthermore two rice seedlings (*Oryza sativa* L, Nipponbare strain) at the two-leaf stage were transplanted in a bundle to the soil and the pot was filled with water to the height of 2 cm over the soil surface. A wettable powder containing the test compound was prepared by the procedure of Formulation Example 3 and diluted with water to a prescribed concentration and the resulting preparation was applied onto the water surface three days after the transplantation of the rice seedlings. The herbicidal effect on the weeds and injury to the paddy rice plant were evaluated 13 days after the application according to the criteria shown in Utility Example 1. The results obtained are shown in Table 5.

TABLE 5

| Test Compound | Amount of compound (g/10a) | Herbicidal effect |  |  |  | Injury to the paddy rice plant |
|---|---|---|---|---|---|---|
| | | Barnyard grass | Toothcup | Umbrella plant | Hardstem bulrush | |
| Compound (21) | 50 | 5 | 5 | 5 | 5 | — |
| | 100 | 5 | 5 | 5 | 5 | — |
| | 250 | 5 | 5 | 5 | 5 | — |
| Compound (22) | 50 | 5 | 5 | 5 | 4.5 | — |
| | 100 | 5 | 5 | 5 | 5 | — |
| | 250 | 5 | 5 | 5 | 5 | — |
| Compound (23) | 50 | 4.5 | 5 | 4 | 2 | — |
| | 100 | 5 | 5 | 5 | 2 | — |
| | 250 | 5 | 5 | 5 | 3 | — |
| Compound (25) | 50 | 4.5 | 5 | 3 | 2 | — |
| | 100 | 4.5 | 5 | 4 | 3.5 | — |
| | 250 | 5 | 5 | 5 | 4.5 | — |
| Compound (27) | 50 | 4 | 5 | 4 | 3.5 | — |
| | 100 | 5 | 5 | 5 | 4 | — |
| | 250 | 5 | 5 | 5 | 5 | — |
| Compound (31) | 50 | 5 | 5 | 4 | 2 | — |
| | 100 | 5 | 5 | 5 | 3 | — |
| | 250 | 5 | 5 | 5 | 4 | — |
| Compound (32) | 50 | 4 | 5 | 5 | 1.5 | — |
| | 100 | 5 | 5 | 5 | 3 | — |
| | 250 | 5 | 5 | 5 | 4 | — |
| Compound (33) | 50 | 5 | 4.5 | 5 | 1 | — |

TABLE 5-continued

| Test Compound | Amount of compound (g/10a) | Herbicidal effect | | | | Injury to the paddy rice plant |
|---|---|---|---|---|---|---|
| | | Barnyard grass | Toothcup | Umbrella plant | Hardstem bulrush | |
| | 100 | 5 | 5 | 5 | 2.5 | — |
| | 250 | 5 | 5 | 5 | 4 | — |
| Untreated control | 0 | 0 | 0 | 0 | 0 | — |

UTILITY EXAMPLE 6

Submerged Soil Treatment

Paddy field soil was placed in a pot 10 cm in diameter and sowed with barnyard grass (*Echinochloa crus-galli*), toothcup (*Rotala indica*), umbrella plant (*Cyperus difformis*) and hardstem bulrush (*Scirpus juncoides*). Furthermore two rice seedlings (*Oryza sativa* L, Nipponbare strain) at the two-leaf stage were transplanted in a bundle to the soil and the pot was filled with water to the height of 2 cm over the soil surface. A wettable powder containing the test compound was prepared by the procedure of Formulation Example 3 and diluted with water to a prescribed concentration and the resulting preparation was applied onto the water surface three days after the transplantation of the rice seedlings. The herbicidal effect on the weeds and injury to the paddy rice plant were evaluated 13 days after the application according to the criteria shown in Utility Example 1. The results obtained are shown in Table 6.

wheat (*Triticum aestivum* L.), sawa millet (*Panicum crus-galli* L.), large crab-grass (*Digitaria adscendens* HENR.), Japanese radish (*Raphanus sativus* L.), green gram (*Phaseolus aureus* ROXB.) and wild aramanth (*Amaranthus lividus* L.), and covered with a 1 cm thick layer of soil. A wettable powder containing Compound (21), which was prepared by the procedure of Formulation Example 3, was diluted to a prescribed concentration. The resulting preparation was applied to the stems and leaves by spraying with 1.5 ml of water per pot when the Gramineae plants reached the two-leaf stage. The phytotoxic effect was evaluated 10 days after the application according to the criteria shown below. The results obtained are shown in Table 7.

Criteria for evaluation of phytotoxic effect:

Inhibition of growth, or withering, of plants as compared with the untreated control 5: 80% to 100%
4: Not less than 60% but less than 80%

TABLE 6

| Test Compound | Amount of compound (g/10a) | Herbicidal effect | | | | Injury to the paddy rice plant |
|---|---|---|---|---|---|---|
| | | Barnyard grass | Toothcup | Umbrella plant | Hardstem bulrush | |
| Compound (24) | 250 | 5 | 5 | 4 | 3 | — |
| | 500 | 5 | 5 | 5 | 4 | — |
| | 1000 | 5 | 5 | 5 | 4 | — |
| Compound (26) | 250 | 3 | 5 | 4 | 3 | — |
| | 500 | 4 | 5 | 4 | 4 | — |
| | 1000 | 4.5 | 5 | 5 | 5 | — |
| Compound (28) | 250 | 3 | 4 | 4 | 3.5 | — |
| | 500 | 4 | 5 | 4.5 | 4 | — |
| | 1000 | 5 | 5 | 5 | 5 | — |
| Compound (30) | 250 | 4 | 4 | 4 | 4 | — |
| | 500 | 4.5 | 5 | 5 | 4 | — |
| | 1000 | 5 | 5 | 5 | 5 | — |
| Compound (34) | 250 | 4 | 5 | 4.5 | 4 | — |
| | 500 | 5 | 5 | 5 | 4.5 | — |
| | 1000 | 5 | 5 | 5 | 5 | — |
| Untreated control | 0 | 0 | 0 | 0 | 0 | — |

UTILITY EXAMPLE 7

Foliage Treatment

Sieved cultivated field soil was placed in a porcelain pot 9 cm in diameter, sowed with rice (*Oryza sativa* L.), 3: Not less than 40% but less than 60%
2: Not less than 20% but less than 40%
1: Less than 20%
0: 0%

TABLE 7

| Amount of compound (g/10a) | Test plant | | | | | | | Phytotoxic symptoms |
|---|---|---|---|---|---|---|---|---|
| | Rice | Wheat | Sawa millet | Large crab-grass | Japanese radish | Green gram | Wild aramanth | |
| 250 | 0 | 0 | 3.5 | 4 | 1 | 0 | 5 | Browning |
| 500 | 0 | 0 | 4 | 4.5 | 2 | 0 | 5 | and |
| 1000 | 1 | 1 | 5 | 5 | 2.5 | 0 | 5 | withered leaves |
| Untreated control | 0 | 0 | 0 | 0 | 0 | 0 | 0 | — |

UTILITY EXAMPLE 8

Cultivated Soil Treatment

Sieved cultivated field soil was placed in a porcelain pot 9 cm in diameter, sowed with rice (*Oryza sativa* L.), wheat (*Triticum aestivum* L.), sawa millet (*Panicum crus-galli* L.), large crab-grass (*Digitaria adscendens* HENR.), Japanese radish (*Raphanus sativus* L.), green gram (*Rhaseolus aureus* ROXB.) and wild aramanth (*Amaranthus lividus* L.), and covered with a 1 cm thick layer of soil. A wettable powder containing Compound (21), which was prepared by the procedure of Formulation Example 3, was diluted to a prescribed concentration. Immediately after the covering, the soil was treated with the above obtained preparation using 2 ml of water per pot. The phytotoxic effect was evaluated 13 days thereafter according to the criteria shown in Utility Example 7. The results obtained are shown in Table 8.

and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of *Cyperus serotinus* and arrowhead (*Sagittaria pygmaea*) were transplanted to the soil after forced sprouting. Then two rice seedlings (*Oryza sativa* L, Nipponbare strain) at the two-leaf stage were transplanted in a bundle to the soil and the pot was filled with water to the height of 2 cm over the soil surface. A wettable powder containing the test compound was prepared by the procedure of Formulation Example 2 and diluted with water to a prescribed concentration and the resulting preparation was applied onto the water surface three days after the transplantation of the rice seedlings. The herbicidal effect on the weeds and injury to the paddy rice plant (growth inhibition of the paddy rice plant) were evaluated 20 days after the application according to the criteria shown in Utility Example 1. The results obtained are shown in Table 9.

TABLE 8

| Amount of compound (g/10a) | Rice | Wheat | Sawa millet | Large crab-grass | Japanese radish | Green gram | Wild aramanth | Phytotoxic symptoms |
|---|---|---|---|---|---|---|---|---|
| 100 | 0 | 0 | 3 | 4 | 0 | 0 | 4.5 | Browning |
| 200 | 0 | 0 | 4.5 | 5 | 0 | 0 | 5 | and |
| 400 | 0 | 0 | 5 | 5 | 0 | 0 | 5 | growth |
| 800 | 0.5 | 0.5 | 5 | 5 | 0 | 0 | 5 | inhibition |
| Untreated control | 0 | 0 | 0 | 0 | 0 | 0 | 0 | — |

UTILITY EXAMPLE 9

Submerged Soil Treatment

Sieved paddy field soil was placed in a porcelain pot 12 cm in diameter and, after addition of water, plowed

TABLE 9

| Test compound & amount (g/10a) | | Herbicidal effect | | | | | | | Injury to the paddy rice plant |
|---|---|---|---|---|---|---|---|---|---|
| Compound (21) | Compound (a) | Barnyard grass | Monochoria | Toothcup | Umbrella plant | Hardstem bulrush | *Cyperus serotinus* | Arrowhead | |
| 12.5 | 0 | 4.5 | 5 | 5 | 5 | 3 | 2 | 0.5 | 0 |
| 25 | 0 | 5 | 5 | 5 | 5 | 4.5 | 3 | 0.5 | 0 |
| 50 | 0 | 5 | 5 | 5 | 5 | 5 | 4 | 1 | 0 |
| 100 | 0 | 5 | 5 | 5 | 5 | 5 | 4.5 | 1.5 | 0 |
| 200 | 0 | 5 | 5 | 5 | 5 | 5 | 5 | 2 | 0 |
| 0 | 12.5 | 0 | 0.5 | 0.5 | 1 | 1 | 0 | 0 | 0 |
| 0 | 25 | 0 | 3 | 3 | 2.5 | 3.5 | 0.5 | 1 | 0 |
| 0 | 50 | 0.5 | 4.5 | 5 | 5 | 4 | 2 | 2 | 0 |
| 0 | 100 | 1 | 5 | 5 | 5 | 4.5 | 3 | 3.5 | 0.5 |
| 0 | 200 | 1 | 5 | 5 | 5 | 5 | 4.5 | 4.5 | 1 |
| 12.5 | 12.5 | 5 | 5 | 5 | 5 | 5 | 4 | 0.5 | 0 |
| 25 | 12.5 | 5 | 5 | 5 | 5 | 5 | 4.5 | 1 | 0 |
| 50 | 12.5 | 5 | 5 | 5 | 5 | 5 | 5 | 2 | 0 |
| 100 | 12.5 | 5 | 5 | 5 | 5 | 5 | 5 | 3 | 0 |
| 200 | 12.5 | 5 | 5 | 5 | 5 | 5 | 5 | 4 | 0 |
| 12.5 | 25 | 5 | 5 | 5 | 5 | 5 | 4 | 2 | 0 |
| 25 | 25 | 5 | 5 | 5 | 5 | 5 | 4.5 | 3 | 0 |
| 50 | 25 | 5 | 5 | 5 | 5 | 5 | 5 | 3.5 | 0 |
| 100 | 25 | 5 | 5 | 5 | 5 | 5 | 5 | 4 | 0 |
| 200 | 25 | 5 | 5 | 5 | 5 | 5 | 5 | 4 | 0 |
| 12.5 | 50 | 5 | 5 | 5 | 5 | 5 | 4.5 | 2.5 | 0 |
| 25 | 50 | 5 | 5 | 5 | 5 | 5 | 5 | 3 | 0 |
| 50 | 50 | 5 | 5 | 5 | 5 | 5 | 5 | 4 | 0 |
| 100 | 50 | 5 | 5 | 5 | 5 | 5 | 5 | 4.5 | 0 |
| 200 | 50 | 5 | 5 | 5 | 5 | 5 | 5 | 5 | 0 |
| 12.5 | 100 | 5 | 5 | 5 | 5 | 5 | 4.5 | 4 | 0 |
| 25 | 100 | 5 | 5 | 5 | 5 | 5 | 5 | 4 | 0 |
| 50 | 100 | 5 | 5 | 5 | 5 | 5 | 5 | 5 | 0 |
| 100 | 100 | 5 | 5 | 5 | 5 | 5 | 5 | 5 | 0 |
| 200 | 100 | 5 | 5 | 5 | 5 | 5 | 5 | 5 | 0 |
| 12.5 | 200 | 5 | 5 | 5 | 5 | 5 | 5 | 5 | 0 |
| 25 | 200 | 5 | 5 | 5 | 5 | 5 | 5 | 5 | 0 |
| 50 | 200 | 5 | 5 | 5 | 5 | 5 | 5 | 5 | 0 |

TABLE 9-continued

| Test compound & amount (g/10a) | | Herbicidal effect | | | | | | | Injury to the paddy rice plant |
|---|---|---|---|---|---|---|---|---|---|
| Compound (21) | Compound (a) | Barnyard grass | Monochoria | Toothcup | Umbrella plant | Hardstem bulrush | *Cyperus serotinus* | Arrowhead | |
| 100 | 200 | 5 | 5 | 5 | 5 | 5 | 5 | 5 | 0 |
| 200 | 200 | 5 | 5 | 5 | 5 | 5 | 5 | 5 | 0 |
| Untreated control | | 0 | 0 | 0 | 0 | 0 | 0 | 0 | 0 |

UTILITY EXAMPLE 10

Submerged Soil Treatment

Paddy field soil was placed in a porcelain pot 12 cm in diameter and, after addition of water, plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of *Cyperus serotinus* and arrowhead (*Sagittaria pygmaea*) were transplanted to the soil after forced sprouting. Then two rice seedlings (*Oryza sativa* L, Nipponbare strain) at the two-leaf stage were transplanted in a bundle to the soil and the pot was filled with water to the height of 2 cm over the soil surface. A wettable powder containing the test compound was prepared by the procedure of Formulation Example 2 and diluted with water to a prescribed concentration and the resulting preparation was applied onto the water surface on the day after the transplantation of the rice seedlings. The herbicidal effect on the weeds and injury to the paddy rice plant (growth inhibition of the paddy rice plant) were evaluated 18 days after the application according to the criteria shown in Utility Example 1. The results obtained are shown in Table 10.

TABLE 10

| Test compound | Amount of compound (g/10a) | Herbicidal effect | | | | | | | Injury to the paddy rice plant |
|---|---|---|---|---|---|---|---|---|---|
| | | Barnyard grass | Monochoria | Toothcup | Umbrella plant | Hardstem bulrush | *Cyperus serotinus* | Arrowhead | |
| Compound (21) | 12.5 | 4.5 | 5 | 5 | 4.5 | 3 | 2 | 0.5 | 0 |
| | 25 | 5 | 5 | 5 | 5 | 4 | 3 | 0.5 | 0 |
| | 50 | 5 | 5 | 5 | 5 | 5 | 4 | 1 | 0 |
| Compound (b) | 25 | 0 | 1 | 2 | 0 | 1 | 0 | 0.5 | 0 |
| | 50 | 0 | 3 | 3 | 1 | 2 | 0 | 1 | 0 |
| | 100 | 1 | 4 | 4 | 4 | 4.5 | 2 | 3 | 1 |
| Compound (c) | 25 | 0 | 3 | 2 | 2 | 0 | 0 | 1 | 0 |
| | 50 | 0.5 | 4 | 3 | 5 | 2 | 1 | 2 | 0 |
| | 100 | 1 | 4.5 | 5 | 5 | 4 | 2 | 3 | 1.5 |
| Compound (21) + Compound (b) | 12.5 + 50 | 4.5 | 5 | 5 | 5 | 5 | 4.5 | 4 | 0 |
| | 25 + 50 | 5 | 5 | 5 | 5 | 5 | 5 | 4.5 | 0 |
| | 50 + 50 | 5 | 5 | 5 | 5 | 5 | 5 | 5 | 0 |
| Compound (21) + Compound (c) | 12.5 + 50 | 4.5 | 5 | 5 | 5 | 5 | 4 | 4 | 0 |
| | 25 + 50 | 5 | 5 | 5 | 5 | 5 | 4.5 | 4.5 | 0 |
| | 50 + 50 | 5 | 5 | 5 | 5 | 5 | 5 | 5 | 0 |
| Untreated control | 0 | 0 | 0 | 0 | 0 | 0 | 0 | 0 | 0 |

UTILITY EXAMPLE 11

Submerged Soil Treatment

Paddy field soil was placed in a porcelain pot 12 cm in diameter and, after addition of water, plowed and sowed with barnyard grass (*Echinochloa crus-galli*), monochoria (*Monochoria vaginalis*), toothcup (*Rotala indica*) and umbrella plant (*Cyperus difformis*). Furthermore tubers of *Cyperus serotinus* were transplanted to the soil after forced sprouting. The pot was then filled with water to the height of 2 cm over the soil surface. On the next day, a wettable powder containing the test compound, which was prepared by the procedure of Formulation Example 2, was diluted with water to a prescribed concentration and the resulting preparation was applied onto the water surface. The herbicidal effect was evaluated 18 days after the application according to the criteria shown in Utility Example 1. The results obtained are shown in Table 11.

TABLE 11

| Test compound | Amount of compound (g/10a) | Herbicidal effect | | | | |
|---|---|---|---|---|---|---|
| | | Barnyard grass | Monochoria | Toothcup | Umbrella plant | *Cyperus serotinus* |
| Compound (22) | 25 | 5 | 5 | 5 | 5 | 3 |
| | 50 | 5 | 5 | 5 | 5 | 4 |
| | 100 | 5 | 5 | 5 | 5 | 4 |
| Compound (23) | 25 | 2 | 4 | 4 | 2 | 0 |
| | 50 | 4.5 | 5 | 5 | 4 | 0 |
| | 100 | 5 | 5 | 5 | 5 | 1 |
| Compound (25) | 25 | 1 | 3 | 4.5 | 3 | 0 |
| | 50 | 4.5 | 5 | 5 | 3 | 0 |
| | 100 | 5 | 5 | 5 | 4 | 0.5 |
| Compound (27) | 25 | 1 | 5 | 5 | 1 | 0 |
| | 50 | 4 | 5 | 5 | 4 | 0 |
| | 100 | 5 | 5 | 5 | 5 | 1 |
| Compound (31) | 25 | 3 | 5 | 5 | 3 | 0 |

TABLE 11-continued

| Test compound | Amount of compound (g/10a) | Herbicidal effect | | | | |
|---|---|---|---|---|---|---|
| | | Barnyard grass | Monochoria | Toothcup | Umbrella plant | Cyperus serotinus |
| | 50 | 5 | 5 | 5 | 4 | 0 |
| | 100 | 5 | 5 | 5 | 5 | 0 |
| Compound (32) | 25 | 3 | 4 | 4.5 | 2 | 0 |
| | 50 | 4 | 5 | 5 | 5 | 0 |
| | 100 | 5 | 5 | 5 | 5 | 0 |
| Compound (a) | 25 | 0 | 3 | 4 | 2 | 0 |
| | 50 | 0 | 5 | 5 | 5 | 0 |
| | 100 | 2 | 5 | 5 | 5 | 1 |
| Compound (22) + compound (a) | 25 + 50 | 5 | 5 | 5 | 5 | 4 |
| | 50 + 50 | 5 | 5 | 5 | 5 | 4.5 |
| | 100 + 50 | 5 | 5 | 5 | 5 | 5 |
| Compound (23) + compound (a) | 25 + 50 | 4 | 5 | 5 | 5 | 2 |
| | 50 + 50 | 5 | 5 | 5 | 5 | 3 |
| | 100 + 50 | 5 | 5 | 5 | 5 | 4 |
| Compound (25) + compound (a) | 25 + 50 | 3 | 4.5 | 5 | 5 | 1 |
| | 50 + 50 | 5 | 5 | 5 | 5 | 3 |
| | 100 + 50 | 5 | 5 | 5 | 5 | 4 |
| Compound (27) + compound (a) | 25 + 50 | 3 | 5 | 5 | 4.5 | 1 |
| | 50 + 50 | 4.5 | 5 | 5 | 5 | 2 |
| | 100 + 50 | 5 | 5 | 5 | 5 | 4 |
| Compound (31) + compound (a) | 25 + 50 | 4 | 5 | 5 | 4.5 | 0.5 |
| | 50 + 50 | 5 | 5 | 5 | 5 | 1 |
| | 100 + 50 | 5 | 5 | 5 | 5 | 4 |
| Compound (32) + compound (a) | 25 + 50 | 4 | 5 | 5 | 5 | 1 |
| | 50 + 50 | 5 | 5 | 5 | 5 | 2 |
| | 100 + 50 | 5 | 5 | 5 | 5 | 3.5 |
| Untreated control | 0 | 0 | 0 | 0 | 0 | 0 |

UTILITY EXAMPLE 12

Outdoor Pot Test (Treatment with Granular Composition)

Sieved cultivated field soil was placed in a 1/5,000 are Wagner pot and, after addition of water, plowed and sowed with barnyard grass (*Echinochloa crus-galli*), monochoria (*Monochoria vaginalis*), toothcup (*Rotala indica*) and umbrella plant (*Cyperus difformis*). Furthermore tubers of *Cyperus serotinus* and arrowhead (*Sagittaria pygmaea*) were transplanted to the soil after forced sprouting. Then two rice seedlings (*Oryza sativa* L, Nipponbare strain) at the two-leaf stage were transplanted in a bundle to the soil and the pot was filled with water to the height of 3 cm over the soil surface. Three days after the transplantation of the rice seedlings, a prescribed amount of a granular composition containing Compound (21) and Compound (a), which was prepared by the procedure of Formulation Example 7, was applied onto the water surface. The herbicidal effect on the weeds and injury to the paddy rice plant (inhibition of growth of the paddy rice plant) were evaluated 20 days after the application according to the criteria shown in Utility Example 1. The results obtained are shown in Table 12.

TABLE 12

| Amount of granular composition (kg/10a) | Herbicidal effect | | | | | | Injury to the paddy rice plant |
|---|---|---|---|---|---|---|---|
| | Barnyard grass | Monochoria | Toothcup | Umbrella plant | Cyperus serotinus | Arrowhead | |
| 1 | 5 | 5 | 5 | 5 | 4.5 | 4 | 0 |
| 2 | 5 | 5 | 5 | 5 | 5 | 5 | 0 |
| 3 | 5 | 5 | 5 | 5 | 5 | 5 | 0 |

UTILITY EXAMPLE 13

Outdoor Vat Test (Treatment with Wettable Powder)

Paddy field soil was placed in a 800 cm² vat and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of arrowhead (*Sagittaria pygmaea*) and *Cyperus serotinus* were embedded in the soil. The two rice seedlings (*Oryza sativa* L, Nipponbare strain) at the 2.5-leaf stage were transplanted in a bundle to the soil and the pot was filled with water to the height of 3 cm over the soil surface. A wettable power containing Compound (22) and Compound (b), which was prepared by the procedure of Formulation Example 6, was diluted with water to a prescribed concentration and the resulting preparation was applied onto the water surface three days after the transplantation of the rice seedlings. The herbicidal effect on the weeds and injury to the paddy rice plant were evaluated 14 days after the application according to the criteria shown in Utility Example 1. The results obtained are shown in Table 13.

TABLE 13

| Amount of wettable powder (g/10a) | Herbicidal effect | | | | | | Injury to the paddy rice plant |
|---|---|---|---|---|---|---|---|
| | Barnyard grass | Tooth-cup | Umbrella plant | Hardstem bulrush | Arrow-head | *Cyperus serotinus* | |
| 200 | 5 | 5 | 5 | 5 | 3 | 4 | 0 |
| 400 | 5 | 5 | 5 | 5 | 4.5 | 4.5 | 0 |
| 800 | 5 | 5 | 5 | 5 | 5 | 4.5 | 0 |
| 1000 | 5 | 5 | 5 | 5 | 5 | 5 | 0 |

UTILITY EXAMPLE 14

Test for Phytotoxicity of a Mixture of Compound (27) and Compound (a) to Root of Paddy Rice Plant Sieved paddy field soil was placed in a porcelain pot 9 cm in diameter and, after addition of water, plowed. Thereto were transplanted two rice seedlings (*Oryza sativa* L, Nipponbare strain) at the two-leaf stage in a bundle to the depth of 1 cm, and the pot was filled with water to the height of 2 cm over the soil surface. Three days after the transplantation of the rice seedlings, a wettable powder containing the test compound, which was prepared by the procedure of Formulation Example 2, was diluted with water to a prescribed concentration and the resulting preparation was applied onto the water surface. Twenty days after the application, the root of the paddy rice plant was examined for phytotoxicity. The injury was evaluated according to the criteria shown in Utility Example 1. The results obtained are shown in Table 14.

TABLE 14

| Test compound and amount (g/10a) | | Compound (27) | | | | | |
|---|---|---|---|---|---|---|---|
| | | 0 | 12.5 | 25 | 50 | 100 | 200 |
| Compound (a) | 0 | 0 | 0 | 0 | 0 | 0 | 0 |
| | 100 | 2 | 1 | 0 | 0 | 0 | 0 |
| | 200 | 4 | 2 | 0.5 | 0.5 | 0 | 0 |
| | 400 | 4.5 | 2.5 | 1 | 0.5 | 0.5 | 0.5 |

UTILITY EXAMPLE 15

Submerged Soil Treatment

Sieved paddy field soil was placed in a porcelain pot 12 cm in diameter and, after addition of water, plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of *Cyperus serotinus* and arrowhead (*Sagittaria pygmaea*) were transplanted after forced sprouting. Then two rice seedlings (*Oryza sativa* L, Nipponbare strain) at the two-leaf stage were transplanted in a bundle and the pot was filed with water to the height of 2 cm over the soil surface. A wettable powder containing the test compound, which was prepared by the procedure of Formulation Example 2, was diluted with water to a prescribed concentration and the resulting preparation was applied onto the water surface three days after the transplantation of the rice seedlings. The herbicidal effect on the weeds and injury to the paddy rice plant (inhibition of growth of the paddy rice plant) were evaluated 22 days after the application according to the criteria shown in Utility Example 1. The results obtained are shown in Table 15.

TABLE 15

| Test compound & amount (g/10a) | | Herbicidal effect | | | | | | | Injury to the paddy rice plant |
|---|---|---|---|---|---|---|---|---|---|
| Compound (21) | Compound (d) | Barnyard grass | Monochoria | Toothcup | Umbrella plant | Hardstem bulrush | *Cyperus serotinus* | Arrowhead | |
| 12.5 | 0 | 4.5 | 4 | 4 | 4 | 0 | 1 | 0 | 0 |
| 25 | 0 | 5 | 5 | 5 | 5 | 0.5 | 1 | 0 | 0 |
| 50 | 0 | 5 | 5 | 5 | 5 | 0.5 | 3 | 0 | 0 |
| 100 | 0 | 5 | 5 | 5 | 5 | 2 | 4.5 | 0 | 0 |
| 200 | 0 | 5 | 5 | 5 | 5 | 2 | 4.5 | 0.5 | 0 |
| 0 | 12.5 | 0.5 | 0 | 0 | 0.5 | 0 | 0 | 0 | 0 |
| 0 | 25 | 1 | 0 | 0 | 2 | 0.5 | 0.5 | 0 | 0 |
| 0 | 50 | 1.5 | 2 | 2 | 4 | 2 | 1 | 2.5 | 0 |
| 0 | 100 | 4 | 4.5 | 4.5 | 5 | 3 | 3 | 4 | 0 |
| 0 | 200 | 4.5 | 5 | 5 | 5 | 3.5 | 3.5 | 4.5 | 0 |
| 12.5 | 12.5 | 5 | 4.5 | 4.5 | 4.5 | 0.5 | 2 | 0 | 0 |
| 12.5 | 25 | 5 | 5 | 5 | 5 | 1 | 4.5 | 1 | 0 |
| 12.5 | 50 | 5 | 5 | 5 | 5 | 3 | 4.5 | 4 | 0 |
| 12.5 | 100 | 5 | 5 | 5 | 5 | 4 | 5 | 4.5 | 0 |
| 12.5 | 200 | 5 | 5 | 5 | 5 | 4 | 5 | 5 | 0 |
| 25 | 12.5 | 5 | 5 | 5 | 5 | 1.5 | 4.5 | 1 | 0 |
| 25 | 25 | 5 | 5 | 5 | 5 | 2 | 4.5 | 3 | 0 |
| 25 | 50 | 5 | 5 | 5 | 5 | 3 | 5 | 4.5 | 0 |
| 25 | 100 | 5 | 5 | 5 | 5 | 4 | 5 | 5 | 0 |
| 25 | 200 | 5 | 5 | 5 | 5 | 4.5 | 5 | 5 | 0 |
| 50 | 12.5 | 5 | 5 | 5 | 5 | 2 | 4.5 | 2 | 0 |
| 50 | 25 | 5 | 5 | 5 | 5 | 3 | 5 | 3 | 0 |
| 50 | 50 | 5 | 5 | 5 | 5 | 4 | 5 | 4.5 | 0 |
| 50 | 100 | 5 | 5 | 5 | 5 | 4.5 | 5 | 5 | 0 |
| 50 | 200 | 5 | 5 | 5 | 5 | 5 | 5 | 5 | 0 |
| 100 | 12.5 | 5 | 5 | 5 | 5 | 3 | 5 | 3 | 0 |
| 100 | 25 | 5 | 5 | 5 | 5 | 4 | 5 | 4 | 0 |

TABLE 15-continued

| Test compound & amount (g/10a) | | Herbicidal effect | | | | | | | Injury to the paddy rice plant |
|---|---|---|---|---|---|---|---|---|---|
| Compound (21) | Compound (d) | Barnyard grass | Monochoria | Toothcup | Umbrella plant | Hardstem bulrush | Cyperus serotinus | Arrowhead | |
| 100 | 50 | 5 | 5 | 5 | 5 | 4.5 | 5 | 5 | 0 |
| 100 | 100 | 5 | 5 | 5 | 5 | 5 | 5 | 5 | 0 |
| 100 | 200 | 5 | 5 | 5 | 5 | 5 | 5 | 5 | 0 |
| 200 | 12.5 | 5 | 5 | 5 | 5 | 4 | 5 | 4 | 0 |
| 200 | 25 | 5 | 5 | 5 | 5 | 5 | 5 | 5 | 0 |
| 200 | 50 | 5 | 5 | 5 | 5 | 5 | 5 | 5 | 0 |
| 200 | 100 | 5 | 5 | 5 | 5 | 5 | 5 | 5 | 0 |
| 200 | 200 | 5 | 5 | 5 | 5 | 5 | 5 | 5 | 0 |
| Untreated control | | 0 | 0 | 0 | 0 | 0 | 0 | 0 | 0 |

The herbicidal effects on *Cyperus serotinus* and arrowhead are excerpted from Table 15 and shown in Table 15-1 and Table 15-2, respectively.

TABLE 15-1

(Herbicidal effect on *Cyperus serotinus*)

| Test compound and amount (g/10a) | Compound (21) | | | | | |
|---|---|---|---|---|---|---|
| | | 0 | 12.5 | 25 | 50 | 100 | 200 |
| Compound (d) | 0 | 0 | 1 | 1 | 3 | 4.5 | 4.5 |
| | 12.5 | 0 | 2 | 4.5 | 4.5 | 5 | 5 |
| | 25 | 0.5 | 4.5 | 4.5 | 5 | 5 | 5 |
| | 50 | 1 | 4.5 | 5 | 5 | 5 | 5 |
| | 100 | 3 | 5 | 5 | 5 | 5 | 5 |
| | 200 | 3.5 | 5 | 5 | 5 | 5 | 5 |

TABLE 15-2

(Herbicidal effect on arrowhead)

| Test compound and amount (g/10a) | Compound (21) | | | | | |
|---|---|---|---|---|---|---|
| | | 0 | 12.5 | 25 | 50 | 100 | 200 |
| Compound (d) | 0 | 0 | 0 | 0 | 0 | 0 | 0.5 |
| | 12.5 | 0 | 0 | 1 | 2 | 3 | 4 |
| | 25 | 0 | 1 | 3 | 3 | 4 | 5 |
| | 50 | 2.5 | 4 | 4.5 | 4.5 | 5 | 5 |
| | 100 | 4 | 4.5 | 5 | 5 | 5 | 5 |
| | 200 | 4.5 | 5 | 5 | 5 | 5 | 5 |

UTILITY EXAMPLE 16

Submerged Soil Treatment

Sieved paddy field soil was placed in a porcelain pot 12 cm in diameter and, after addition of water, plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of *Cyperus serotinus* and arrowhead (*Sagittaria pygmaea*) were transplanted after forced sprouting. In addition, two rice seedlings (*Oryza sativa* L, Nipponbare strain) at the two-leaf stage were transplanted in a bundle to the soil and the pot was filled with water to the height of 2 cm over the soil surface. A wettable power containing the test compound, which was prepared by the procedure of Formulation Example 2, was diluted with water to a prescribed concentration and the resulting preparation was applied onto the water surface three days after the transplantation of the rice seedlings. The herbicidal effect on the weeds and injury to the paddy rice plant (inhibition of growth of the paddy rice plant) were evaluated 22 days after the application according to the criteria shown in Utility Example 1. The results obtained are shown in Table 16.

TABLE 16

| Test compound & amount (g/10a) | | Herbicidal effect | | | | | | | Injury to the paddy rice plant |
|---|---|---|---|---|---|---|---|---|---|
| Compound (2) | Compound (e) | Barnyard grass | Monochoria | Toothcup | Umbrella plant | Hardstem bulrush | Cyperus serotinus | Arrowhead | |
| 12.5 | 0 | 4.5 | 3 | 4 | 2.5 | 0 | 2.5 | 0 | 0 |
| 25 | 0 | 4.5 | 4 | 4.5 | 4 | 0.5 | 4 | 0 | 0 |
| 50 | 0 | 5 | 5 | 4.5 | 4.5 | 0.5 | 4.5 | 0 | 0 |
| 100 | 0 | 5 | 5 | 5 | 5 | 1 | 4.5 | 0 | 0 |
| 200 | 0 | 5 | 5 | 5 | 5 | 1 | 5 | 0 | 0 |
| 0 | 12.5 | 0 | 0 | 0 | 0.5 | 0 | 0 | 0 | 0 |
| 0 | 25 | 1 | 0.5 | 1 | 1 | 1 | 0.5 | 0.5 | 0 |
| 0 | 50 | 2 | 2 | 2 | 3 | 2 | 1 | 3 | 0 |
| 0 | 100 | 4 | 4 | 3 | 4.5 | 3 | 2 | 4 | 0 |
| 0 | 200 | 4.5 | 5 | 5 | 5 | 4 | 3.5 | 4.5 | 0 |
| 12.5 | 12.5 | 5 | 4 | 4.5 | 4 | 0.5 | 3 | 0 | 0 |
| 12.5 | 25 | 5 | 4.5 | 5 | 5 | 1 | 4.5 | 0.5 | 0 |
| 12.5 | 50 | 5 | 5 | 5 | 5 | 2.5 | 5 | 3 | 0 |
| 12.5 | 100 | 5 | 5 | 5 | 5 | 4 | 5 | 4.5 | 0 |
| 12.5 | 200 | 5 | 5 | 5 | 5 | 4.5 | 5 | 5 | 0 |
| 25 | 12.5 | 5 | 4.5 | 5 | 5 | 1 | 4 | 0.5 | 0 |
| 25 | 25 | 5 | 5 | 5 | 5 | 1.5 | 4.5 | 1 | 0 |
| 25 | 50 | 5 | 5 | 5 | 5 | 3 | 5 | 4 | 0 |
| 25 | 100 | 5 | 5 | 5 | 5 | 4 | 5 | 5 | 0 |
| 25 | 200 | 5 | 5 | 5 | 5 | 5 | 5 | 5 | 0 |
| 50 | 12.5 | 5 | 5 | 5 | 5 | 1.5 | 4.5 | 1 | 0 |
| 50 | 25 | 5 | 5 | 5 | 5 | 2 | 5 | 2 | 0 |
| 50 | 50 | 5 | 5 | 5 | 5 | 3.5 | 5 | 4 | 0 |
| 50 | 100 | 5 | 5 | 5 | 5 | 5 | 5 | 5 | 0 |
| 50 | 200 | 5 | 5 | 5 | 5 | 5 | 5 | 5 | 0 |
| 100 | 12.5 | 5 | 5 | 5 | 5 | 2 | 4.5 | 1 | 0 |
| 100 | 25 | 5 | 5 | 5 | 5 | 3 | 5 | 3 | 0 |
| 100 | 50 | 5 | 5 | 5 | 5 | 4 | 5 | 4 | 0 |

TABLE 16-continued

| Test compound & amount (g/10a) | | Herbicidal effect | | | | | | | Injury to the paddy rice plant |
|---|---|---|---|---|---|---|---|---|---|
| Compound (2) | Compound (e) | Barnyard grass | Monochoria | Toothcup | Umbrella plant | Hardstem bulrush | Cyperus serotinus | Arrowhead | |
| 100 | 100 | 5 | 5 | 5 | 5 | 5 | 5 | 5 | 0 |
| 100 | 200 | 5 | 5 | 5 | 5 | 5 | 5 | 5 | 0 |
| 200 | 12.5 | 5 | 5 | 5 | 5 | 3 | 5 | 2 | 0 |
| 200 | 25 | 5 | 5 | 5 | 5 | 4 | 5 | 4 | 0 |
| 200 | 50 | 5 | 5 | 5 | 5 | 5 | 5 | 5 | 0 |
| 200 | 100 | 5 | 5 | 5 | 5 | 5 | 5 | 5 | 0 |
| 200 | 200 | 5 | 5 | 5 | 5 | 5 | 5 | 5 | 0 |
| Untreated control | | 0 | 0 | 0 | 0 | 0 | 0 | 0 | 0 |

The herbicidal effects on *Cyperus serotinus* and arrowhead are excerpted from Table 16 and shown in Table 16-1 Table 16-2, respectively.

TABLE 16-1

(Herbicidal effect on *Cyperus serotinus*)

| Test compound and amount (g/10a) | | Compound (22) | | | | |
|---|---|---|---|---|---|---|
| | | 0 | 12.5 | 25 | 50 | 100 | 200 |
| Compound (e) | 0 | 0 | 2.5 | 4 | 4.5 | 4.5 | 5 |
| | 12.5 | 0 | 3 | 4 | 4.5 | 4.5 | 5 |
| | 25 | 0.5 | 4.5 | 4.5 | 5 | 5 | 5 |
| | 50 | 1 | 5 | 5 | 5 | 5 | 5 |
| | 100 | 2 | 5 | 5 | 5 | 5 | 5 |
| | 200 | 3.5 | 5 | 5 | 5 | 5 | 5 |

TABLE 16-2

(Herbicidal effect on arrowhead)

| Test compound and amount (g/10a) | | Compound (22) | | | | |
|---|---|---|---|---|---|---|
| | | 0 | 12.5 | 25 | 50 | 100 | 200 |
| Compound (e) | 0 | 0 | 0 | 0 | 0 | 0 | 0 |
| | 12.5 | 0 | 0 | 0.5 | 1 | 1 | 2 |
| | 25 | 0.5 | 0.5 | 1 | 2 | 3 | 4 |
| | 50 | 3 | 3 | 4 | 4 | 4 | 5 |
| | 100 | 4 | 4.5 | 5 | 5 | 5 | 5 |
| | 200 | 4.5 | 5 | 5 | 5 | 5 | 5 |

UTILITY EXAMPLE 17

Submerged Soil Treatment

Sieved paddy field soil was placed in a porcelain pot 12 cm in diameter and, after addition of water, plowed and sowed with barnyard grass (*Echinochloa crus-galli*), broad-leaved weeds [monochoria (*Monochoria vaginalis*) and toothcup (*Rotala indica*)] and hardstem bulrush (*Scirpus juncoides*). Tubers of *Cyperus serotinus* and arrowhead (*Sagittaria pygmaea*) were transplanted after forced sprouting. Furthermore two rice seedlings (*Oryza sativa* L, Nipponbare strain) at the two-leaf stage were transplanted in a bundle to the soil and the pot was filled with water to the height of 2 cm over the soil surface. A wettable powder containing the test compound, which was prepared by the procedure of Formulation Example 2, was diluted with water to a prescribed concentration and the resulting preparation was applied onto the water surface three days after the transplantation of the rice seedlings. The herbicidal effect on the weeds and injury to the paddy rice plant (inhibition of growth of the paddy rice plant) were evaluated 20 days after the application according to the criteria shown in Utility Example 1. The results obtained are shown in Table 17

TABLE 17

| Test compound | Amount of compound (g/10a) | Herbicidal effect | | | | |
|---|---|---|---|---|---|---|
| | | Barnyard grass | Broad-leaved weeds | Hardstem bulrush | Cyperus serotinus | Arrowhead |
| Compound (23) | 25 | 3.5 | 5 | 0 | 1 | 0 |
| Compound (24) | 25 | 3.5 | 2.5 | 0.5 | 4.5 | 0 |
| Compound (25) | 25 | 3.5 | 3 | 0 | 4.5 | 0 |
| Compound (26) | 100 | 3 | 1 | 0 | 1.5 | 0 |
| Compound (27) | 25 | 2 | 2 | 0 | 4.5 | 0 |
| Compound (28) | 500 | 1 | 2 | 0 | 0 | 0 |
| Compound (29) | 100 | 4.5 | 4.5 | 0 | 0 | 0 |
| Compound (30) | 100 | 2 | 0.5 | 1.5 | 4.5 | 1 |
| Compound (31) | 25 | 4 | 4.5 | 0 | 4.5 | 0 |
| Compound (32) | 25 | 4 | 4 | 0 | 4.5 | 0 |
| Compound (d) | 50 | 1.5 | 2 | 2 | 1 | 2.5 |
| Compound (23) + compound (d) | 25 + 50 | 5 | 5 | 3 | 4 | 3 |
| Compound (24) + compound (d) | 25 + 50 | 5 | 5 | 4 | 5 | 3 |
| Compound (25) + compound (d) | 25 + 50 | 5 | 5 | 4 | 5 | 4 |
| Compound (26) + compound (d) | 100 + 50 | 5 | 4 | 3 | 3 | 3 |
| Compound (27) + compound (d) | 25 + 50 | 4.5 | 5 | 3 | 5 | 3 |
| Compound (28) + compound (d) | 500 + 50 | 4 | 4 | 2.5 | 2.5 | 3 |
| Compound (29) + compound (d) | 100 + 50 | 5 | 5 | 3 | 5 | 4 |
| Compound (30) + compound (d) | 100 + 50 | 4.5 | 4 | 4 | 5 | 4.5 |

TABLE 17-continued

| Test compound | Amount of compound (g/10a) | Herbicidal effect | | | | |
|---|---|---|---|---|---|---|
| | | Barnyard grass | Broad-leaved weeds | Hardstem bulrush | *Cyperus serotinus* | Arrowhead |
| Compound (31) + compound (d) | 25 + 50 | 5 | 5 | 3 | 5 | 4 |
| Compound (32) + compound (d) | 25 + 50 | 5 | 5 | 3.5 | 5 | 4 |
| Untreated control | 0 | 0 | 0 | 0 | 0 | 0 |

What is claimed is:

1. A compound of the general formula

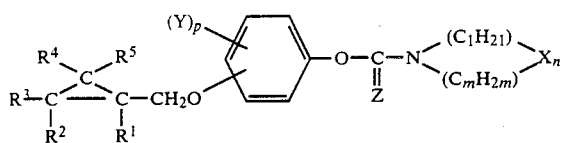

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, $R^4$ and $R^5$ are the same or different and each is a halogen atom, and Z is an oxygen or sulfur atom.

2. The compound of claim 1, wherein said compound is a compound of the general formula

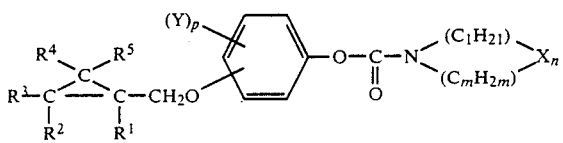

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, and $R^4$ and $R^5$ are the same or different and each is a halogen atom.

3. The compound of claim 1, wherein said compound is a compound of the general formula

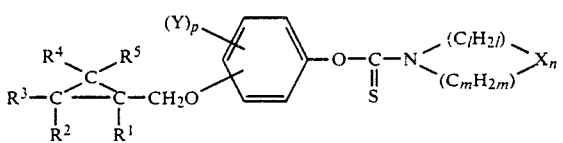

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, and $R^4$ and $R^5$ are the same or different and each is a halogen atom.

4. The compound of claim 1, wherein said compound is a compound of the general formula

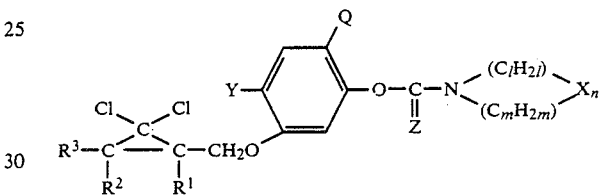

wherein X is a vinylene group, l and m each is an integer of 1 to 4, n is an integer of 0 or 1, the N-heterocycle comprising the nitrogen atom, the two alkylene chains and X is 5- or 6-membered, the two alkylene chains each may be branched, Y is a halogen atom, Q is a hydrogen or halogen atom, $R^1$ is a hydrogen atom or a lower alkyl group, $R^2$ and $R^3$ are the same or different and each is a hydrogen atom or a lower alkyl or phenyl group, and Z is an oxygen or sulfur atom.

5. The compound of claim 1, wherein said compound is 4-chloro-3-[(2,2-dichlorocyclopropyl)methoxy]phenyl 1-pyrrolidinecarboxylate.

6. The compound of claim 1, wherein said compound is 4-chloro-3-[(2,2-dichloro-1-methylcyclopropyl)methoxy]phenyl 1-pyrrolidinecarboxylate.

7. The compound of claim 1, wherein said compound is 4-chloro-3-[(2,2-dichloro-3,3-dimethylcyclopropyl)methoxy]phenyl 1-pyrrolidinecarboxylate.

8. The compound of claim 1, wherein said compound is 4-chloro-3-[(2,2-dichloro-cis-3-methylcyclopropyl)methoxy]phenyl 1-pyrrolidinecarboxylate.

9. The compound of claim 1, wherein said compound is 4-chloro-3[(2,2-dichloro-trans-3-methylcyclopropyl)methoxy]phenyl 1-pyrrolidinecarboxylate.

10. The compound of claim 1, wherein said compound is 2,4-dichloro-5-[(2,2-dichlorocyclopropyl)methoxy]phenyl 1-pyrrolidinecarboxylate.

11. The compound of claim 1, wherein said compound is O-[4-chloro-3-[(2,2-dichlorocyclopropyl)methoxy]phenyl] 1-pyrrolidinecarbothioate.

12. The compound of claim 1, wherein said compound is O-[4-chloro-3-[(2,2-dichloro-1-methylcyclopropyl)methoxy]phenyl] 1-pyrrolidinecarbothioate.

13. A herbicidal composition which comprises (i) a herbicidally effective amount of a compound of the general formula

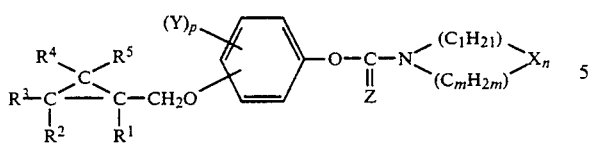

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, $R^4$ and $R^5$ are the same or different and each is a halogen atom, and Z is an oxygen or sulfur atom, and (ii) an inert carrier therefor.

14. The herbicidal composition of claim 13, wherein said compound is a compound of the general formula

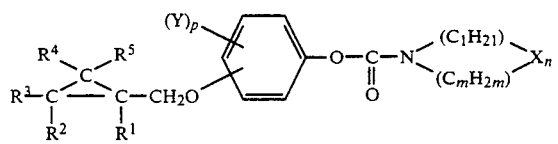

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, and $R^4$ and $R^5$ are the same or different and each is a halogen atom.

15. The herbicial composition of claim 13, wherein said compound is a compound of the general formula

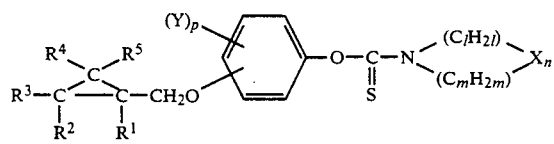

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, and $R^4$ and $R^5$ are the same or different and each is a halogen atom.

16. The herbicidal composition of claim 13, wherein said compound is a compound of the general formula

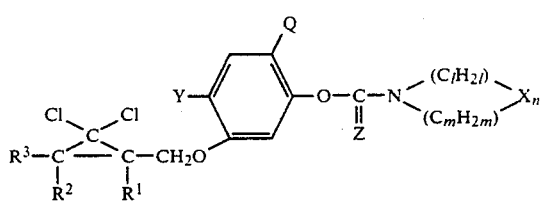

wherein X is a vinylene group, l and m each is an integer of 1 to 4, n is an integer of 0 or 1, the N-heterocycle comprising the nitrogen atom, the two alkylene chains and X is 5- or 6-membered, the two alkylene chains each may be branched, Y is a halogen atom, Q is a hydrogen or halogen atom, $R^1$ is a hydrogen atom or a lower alkyl group, $R^2$ and $R^3$ are the same or different and each is a hydrogen atom or a lower alkyl or phenyl group, and Z is an oxygen or sulfur atom.

17. The herbicidal composition of claim 13, wherein said compound is 4-chloro-3-[(2,2-dichlorocyclopropyl)methoxy]phenyl 1-pyrrolidinecarboxylate.

18. The herbicidal composition of claim 13, wherein said compound is 4-chloro-3-[(2,2-dichloro-1-methylcyclopropyl)methoxy]phenyl 1-pyrrolidinecarboxylate.

19. The herbicidal composition of claim 13, wherein said compound is 4-chloro-3-[(2,2-dichloro-3,3-dimethylcyclopropyl)methoxy]phenyl 1-pyrrolidinecarboxylate.

20. The herbicidal composition of claim 13, wherein said compound is 4-chloro-3-[(2,2-dichloro-cis-3-methylcyclopropyl)methoxy]phenyl 1-pyrrolidinecarboxylate.

21. The herbicidal composition of claim 13, wherein said compound is 4-chloro-3-[(2,2-dichloro-trans-3-methylcyclopropyl)methoxy]phenyl 1-pyrrolidinecarboxylate.

22. The herbicidal composition of claim 13, wherein said compound is 2,4-dichloro-5-[(2,2-dichlorocyclopropyl)methoxy]phenyl 1-pyrrolidinecarboxylate.

23. The herbicidal composition of claim 13, wherein said compound is O-[4-chloro-3-[(2,2-dichlorocyclopropyl)methoxy]phenyl] 1-pyrrolidinecarbothioate.

24. The herbicidal composition of claim 13, wherein said compound is O-[4-chloro-3-[(2,2-dichloro-1-methylcyclopropyl)methoxy]phenyl] 1-pyrrolidinecarbothioate.

25. The herbicidal composition of any of claims 13–24, wherein the content of said compound is at least $1 \times 10^{-3}$ percent by weight based on the total weight of said composition.

26. The herbicidal composition of claim 25, wherein the content of said compound is 0.01 to 95 percent by weight.

27. The herbicidal composition of claim 26, wherein the content of said compound is 0.1 to 80 percent by weight.

28. A method of controlling weeds which comprises applying to the area in which weeds are to be controlled an herbicidally effective amount of a compound of the general formula

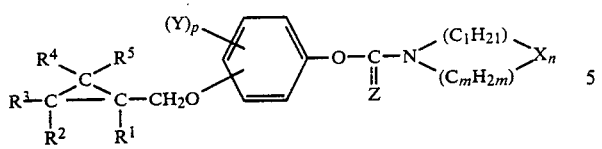

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, $R^4$ and $R^5$ are the same or different and each is a halogen atom, and Z is an oxygen or sulfur atom.

29. The method of claim 28, wherein said compound is a compound of the general formula

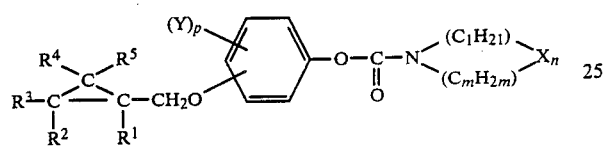

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, and $R^4$ and $R^5$ are the same or different and each is a halogen atom.

30. The method of claim 28, wherein said compound is a compound of the general formula

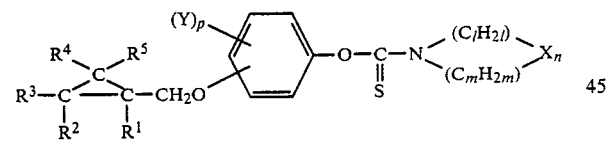

wherein X is a vinylene group, l and m each is an integer of 1 to 4, n is an integer of 0 or 1, the N-heterocycle comprising the nitrogen atom, the two alkylene chains and X is 5- to 7-membered, the two alkylene chains each may be branched, Y is a halogen atom, p is an integer of 1 or 2, $R^1$ is a hydrogen atom or a lower alkyl group, $R^2$ and $R^3$ are the same or different and each is a hydrogen atom or a lower alkyl or phenyl group, and $R^4$ and $R^5$ are the same or different and each is a halogen atom.

31. The method of claim 28, wherein said compound is a compound of the general formula

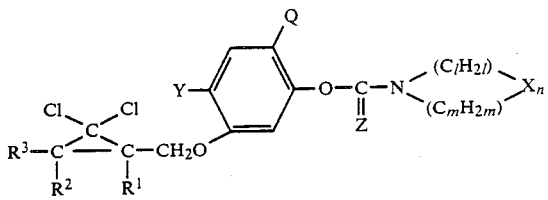

wherein X is a vinylene group, l and m each is an integer of 1 to 4, n is an integer of 0 or 1, the N-heterocycle comprising the nitrogen atom, the two alkylene chains and X is 5- or 6-membered, the two alkylene chains each may be branched, Y is a halogen atom, Q is a hydrogen or halogen atom, $R^1$ is a hydrogen atom or a lower alkyl group, $R^2$ and $R^3$ are the same or different and each is a hydrogen atom or a lower alkyl or phenyl group, and Z is an oxygen or sulfur atom.

32. The method of claim 28, wherein said compound is 4-chloro-3-[(2,2-dichlorocyclopropyl)methoxy]phenyl 1-pyrrolidinecarboxylate.

33. The method of claim 28, wherein said compound is 4-chloro-3-[(2,2-dichloro-1-methylcyclopropyl)methoxy]phenyl 1-pyrrolidinecarboxylate.

34. The method of claim 28, wherein said compound is 4-chloro-3-[(2,2-dichloro-3,3-diemthylcyclopropyl)methoxy]phenyl 1-pyrrolidinecarboxylate.

35. The method of claim 28, wherein said compound is 4-chloro-3-[(2,2-dichloro-cis-3-methylcyclopropyl)methoxy]phenyl 1-pyrrolidinecarboxylate.

36. The method of claim 28, wherein said compound is 4-chloro-3-[(2,2-dichloro-trans-3-methylcyclopropyl)methoxy]-phenyl 1-pyrrolidinecarboxylate.

37. The method of claim 28, wherein said compound is 2,4-dichloro-5-[(2,2-dichlorocyclopropyl)methoxy]phenyl 1-pyrrolidinecarboxylate.

38. The method of claim 28, wherein said compound is O-[4-chloro-3-[(2,2-dichlorocyclopropyl)methoxy]phenyl] 1-pyrolidinecarbothioate.

39. The method of claim 28, wherein said compound is O-[4-chloro-3-[(2,2-dichloro-1-methylcyclopropyl)methoxy]phenyl] 1-pyrrolidinecarbothioate.

40. The method of any of claims 28–39, wherein said compound is applied in an amount of at least 1 gram per 10 ares.

41. The method of claim 40, wherein said compound is applied in an amount of 2.5 to 2,000 grams per 10 ares.

42. The method of claim 41, wherein said compound is applied in an amount of 10 to 1,000 grams per 10 ares.

* * * * *